United States Patent [19]

Berg et al.

[11] Patent Number: 5,531,978
[45] Date of Patent: * Jul. 2, 1996

[54] AMINOPOLYCARBOXYLIC ACIDS AND DERIVATIVES THEREOF

[75] Inventors: Arne Berg, Blommenholm, Norway; Torsten Almén, Malmö, Sweden; Jo Klaveness, Oslo, Norway; Pal Rongved, Hellvik, Norway; Terje Thomassen; Harald Dugstad, both of Oslo, Norway

[73] Assignee: Nycomed Imaging AS, Oslo, Norway

[*] Notice: The term of this patent shall not extend beyond the expiration date of Pat. No. 5,198,208.

[21] Appl. No.: 14,569

[22] Filed: Feb. 8, 1993

Related U.S. Application Data

[63] Continuation-in-part of Ser. No. 457,717, filed as PCT/GB88/00572, Jul. 15, 1988, Pat. No. 5,198,208, and Ser. No. 934,742, filed as PCT/EP91/00674, Apr. 9, 1991, abandoned.

[30] Foreign Application Priority Data

Jul. 16, 1987 [GB] United Kingdom ............... 87 16778
Jul. 17, 1987 [GB] United Kingdom ............... 87 16914
Apr. 9, 1990 [GB] United Kingdom ............... 90 07965

[51] Int. Cl.⁶ ........................... A61K 51/00; A61K 49/00
[52] U.S. Cl. ................. 424/1.11; 424/9.36; 424/9.365; 424/9.42; 424/9.5; 534/10; 534/12; 534/13; 534/14; 534/15; 534/16; 556/45
[58] Field of Search ................. 424/1.11, 9; 534/10, 534/12, 13, 14, 15, 16; 556/45

[56] References Cited

U.S. PATENT DOCUMENTS

| | | |
|---|---|---|
| 2,387,735 | 10/1945 | Bersworth . |
| 2,831,885 | 4/1958 | Kroll et al. . |
| 2,848,469 | 8/1958 | Kroll et al. . |
| 2,894,023 | 7/1959 | Rubin . |
| 2,906,762 | 9/1959 | Knell et al. . |
| 3,407,645 | 9/1946 | Bersworth . |
| 4,639,365 | 1/1987 | Sherry . |
| 4,647,447 | 3/1987 | Gries et al. ................... 424/9 |
| 4,885,363 | 12/1989 | Tweedle et al. ............. 424/2 |
| 4,916,246 | 4/1990 | Felder et al. ............... 534/16 |
| 4,935,518 | 6/1990 | Rocklage et al. ........... 546/6 |
| 5,049,667 | 9/1991 | Schaefer et al. ......... 540/474 |
| 5,198,208 | 3/1993 | Berg et al. ................ 424/1.1 |

FOREIGN PATENT DOCUMENTS

| | | |
|---|---|---|
| 14611/88 | 10/1988 | Australia . |
| 0071564 | 2/1983 | European Pat. Off. . |
| 0130934 | 1/1985 | European Pat. Off. . |
| 0165728 | 12/1985 | European Pat. Off. . |
| 0232751 | 8/1987 | European Pat. Off. . |
| 0230893 | 8/1987 | European Pat. Off. . |
| 0255471 | 2/1988 | European Pat. Off. . |
| 0287465 | 10/1988 | European Pat. Off. . |
| 0292689 | 11/1988 | European Pat. Off. . |
| 1144583 | 10/1957 | France . |
| 2918842 | 12/1979 | Germany . |
| 3401052 | 7/1984 | Germany . |
| 219079 | 8/1988 | New Zealand . |
| 172753 | 7/1965 | U.S.S.R. . |
| 727483 | 4/1955 | United Kingdom . |
| 750481 | 6/1956 | United Kingdom . |
| 2137612 | 10/1984 | United Kingdom . |
| 2169598 | 7/1986 | United Kingdom . |
| 2169599 | 7/1986 | United Kingdom . |
| WO88/08422 | 3/1988 | WIPO . |
| WO88/07521 | 3/1988 | WIPO . |

OTHER PUBLICATIONS

Gavin et al., *Chemical Abstracts*, 104:137019y, 1986.
Samoilova et al., *Chemical Abstracts*, 73:98343u, 1973.

*Primary Examiner*—Philip Tucker
*Attorney, Agent, or Firm*—Bacon & Thomas

[57] ABSTRACT

There are provided chelating agents particularly useful for the preparation of diagnostic and therapeutic agents for magnetic resonance imaging, scintigraphy, ultrasound imaging, radiotherapy and heavy metal detoxification, said agents being compounds of formula I $$X-CHR_1-NZ-(CHR_1)_n-A-(CHR_1)_m-NZ-CHR_1-X \quad (I)$$

wherein n and m are 2, 3 or 4; and A, X, $R_1$ and Z are as defined in the specification.

7 Claims, No Drawings

AMINOPOLYCARBOXYLIC ACIDS AND DERIVATIVES THEREOF

This application is a continuation-in-part of U.S. patent application Ser. No. 07/457,717, filed as PCT/GB88/00572, Jul. 15, 1988 now U.S. Pat. No. 5,198,208 and a continuation-in-part of U.S. patent application Ser. No. 07/934,742, filed as PCT/EP91/00674 Apr. 9, 1991 now abandoned.

The present invention relates to certain chelating agents, in particular aminopoly(carboxylic acid or carboxylic acid derivative) compounds, and to the metal chelates thereof.

The medical use of chelating agents is well established, for example as stabilizers for pharmaceutical preparations, as antidotes for poisonous heavy metal species and as diagnostic agents for the administration of metal species (e.g. ions or atoms) for diagnostic techniques such as X-ray, magnetic resonance imaging (MRI) or ultrasound imaging or scintigraphy.

Aminopoly(carboxylic acid or carboxylic acid derivative) (hereinafter APCA) chelating agents and their metal chelates are well known and are described for example in U.S. Pat. No. 2,407,645(Bersworth), U.S. Pat. No. 2,387,735 (Bersworth), EP-A-71564 (Schering), EP-A-130934 (Schering), EP-A-165728 (Nycomed AS), DE-A-2918842 (Rexolin Chemicals AB) and DE-A-3401052 (Schering).

Thus, for example, EP-A-71564 describes paramagnetic metal chelates, for which the chelating agent is nitrilotriacetic acid (NTA), N,N,N',N'-ethylenediaminetetraacetic acid (EDTA), N-hydroxyethyl-N,N',N'-ethylenediamine-triacetic acid (HEDTA), N,N,N', N'',N''-diethylenetriaminepentaacetic acid (DTPA) and N-hydroxyethylimino-diacetic acid, as being suitable as contrast agents for MRI, contrast being achieved by the effect of the magnetic field of the paramagnetic species (e.g. Gd(III)) with the chelating agents serving to reduce the toxicity and to assist administration of that paramagnetic species.

Amongst the particular metal chelates disclosed by EP-A-71564 was Gd DTPA, the use of which as an MRI contrast agent has recently received much attention. The Gd(III) chelate of 1,4,7,10-tetraazacyclododecanetetraacetic acid (DOTA), referred to in DE-A-3401052 (Schering) and in U.S. Pat. No. 4,639,365 (University of Texas), has also recently received attention in this regard.

To improve stability, water solubility and selectivity, relative to the APCA chelating agents described in EP-A-71564, Schering, in EP-A-130934, have proposed the partial substitution for the N-attached carboxyalkyl groups of alkyl, alkoxyalkyl, alkoxycarbonylalkyl or alkylaminocarbonylalkyl groups, where any amide nitrogens may themselves carry polyhydroxyalkyl groups.

However, all hitherto known APCA chelating agents and their metal chelates encounter problems of toxicity, stability or selectivity and there is thus a general and continuing need for APCA chelating agents which form metal chelates of reduced toxicity or improved stability.

We now propose certain new improved toxicity APCAs, and in particular APCAs which carry hydrophilic groups on the amine nitrogens or on the alkylene chains linking the amine nitrogens.

The disclosures of U.S. patent application Ser. No. 07/934,742 are incorporated herein by reference.

Viewed from one aspect, the present invention thus provides APCA chelating agents wherein at least one bridging group between amine nitrogens carries a hydrophilic moiety, preferably a hydroxyalkyl or an optionally hydroxylated alkoxy group, and metal chelates and salts thereof.

Viewed from another aspect, the present invention provides compounds of formula I

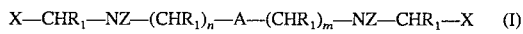

$$X-CHR_1-NZ-(CHR_1)_n-A-(CHR_1)_m-NZ-CHR_1-X \quad (I)$$

(wherein each of the groups Z is a group —$CHR_1X$ or the groups Z together are a group —$(CHR_1)_q$—A'—$(CHR_1)_r$—, where A' is an oxygen or sulphur atom or a group —N—Y; A is a group

$$-N-Y$$

or A—$(CHR_1)_m$— represents a carbon-nitrogen bond or, when the groups Z together are a group —$(CHR_1)_q$—A'—$(CHR_1)_r$—, A may also represent an oxygen or sulphur atom; each Y, which may be the same or different, is a each X, which may be the same or different, is a carboxyl group or a derivative thereof or a group $R_1$; each $R_1$, which may be the same or different, is a hydrogen atom, a hydroxyalkyl group or an optionally hydroxylated alkoxy or alkoxyalkyl group; n,m,p,q and r are each 2,3 or 4, preferably 2; with the provisos that at least two nitrogens carry a —$CHR_1X$ moiety wherein X is a carboxyl group or a derivative thereof, that each —$CHR_1X$ moiety is other than a methyl group, and that unless A' is oxygen or sulphur or A is N—$(CHR_1)_p$—$N(CHR_1X)_2$ at least one $R_1$ is other than hydrogen, preferably also that unless A' is sulphur or A is N—$(CHR_1)_p$—$N(CHR_1X)_2$ at least one $R_1$ is other than hydrogen, preferably also that where A and A' are groups $NCHR_1X$ at least one $CHR_1X$ group is other than a —$CH_2X^3$ group (where $X^3$ represents a carboxyl group or a derivative thereof or a 2-hydroxyethyl or 2,3-dihydroxypropyl group) and preferably also that each nitrogen atom carrying a —$CHR_1X$ moiety wherein X is a carboxyl group or a derivative thereof carries at least one such moiety which is other than a —$CH_2X$ moiety) and metal chelates and salts thereof.

Particularly preferred compounds of formula I include those of-formula Ia

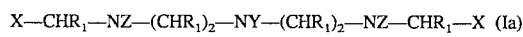

$$X-CHR_1-NZ-(CHR_1)_2-NY-(CHR_1)_2-NZ-CHR_1-X \quad (Ia)$$

(wherein each group Z is a group —$CHR_1X$ or the groups Z together are a group —$(CHR_1)_2$—A'—$(CHR_1)_2$—; each Y, which may be the same or different, is a group —$(CHR_1)_2$—$N(CHR_1X)_2$ or —$CHR_1X$; and A', X and $R_1$ are as hereinbefore defined) and metal chelates and salts thereof.

In the compounds of the present invention, it is particularly preferred that one or more of the —$CHR_1$-groups in the bridges between the amine nitrogens, i.e. in the groups $(CHR_1)_n$, $(CHR_1)_m$, $(CHR_1)_p$, $(CHR_1)_q$ and $(CHR_1)_r$, should carry a hydrophilic $R_1$ group. Prior art APCAs, such as DTPA or DOTA for example, possess certain hydrophobic areas which cause the metal chelates produced from such chelating agents to present relatively lipophilic and hydrophobic zones.

In the compounds of formula I, each hydrophilic $R_1$ group, which may be straight-chained or branched, preferably has a carbon atom content of from 1 to 8, especially preferably 1 to 6, carbon atoms. The $R_1$ groups may be alkoxy, polyalkoxy, polyhydroxy-alkoxy, hydroxyalkoxyalkyl or hydroxypolyalkoxyalkyl groups, but more preferably they will be monohydroxyalkyl or polyhydroxyalkyl groups. The hydrophilic $R_1$ groups serve to increase the hydrophilicity and reduce the lipophilicity of the metal chelates formed with the chelating agents of the invention and it is preferred that the compounds of formula I should contain at least 1, conveniently from 1 to 12, and preferably 2 to 8 hydrophilic $R_1$ groups and that in total the hydrophilic $R_1$ groups should contain about 6 or more hydroxy or ether oxygen atoms.

As hydrophilic $R_1$ groups, the compounds of the invention may thus include for example hydroxymethyl, 2-hydroxyethyl, 1,2-dihydroxyethyl, 3-hydroxypropyl, 2,3-dihydroxypropyl, 2,3,4-trihydroxybutyl, 1-(hydroxymethyl)-2-hydroxy-ethyl, methoxymethyl, ethoxymethyl, 2-hydroxyethoxymethyl, methoxyethoxymethyl, (2-hydroxy-ethoxy)ethyl, etc., groups.

The carboxyl derivatives which may be represented by the groups X in the compounds of formula I, may include, for example, amide groups, ester groups and carboxylate salt groups, for example groups of formulae —$CONR_2R_3$ (wherein $R_2$ is a hydrogen atom or an optionally hydroxylated alkyl, for example $C_{1-6}$ alkyl, group and $R_3$ is a hydrogen atom, a hydroxyl group or an optionally hydroxylated alkyl group), —$COOR_4$ (wherein $R_4$ is an optionally hydroxylated alkyl group), and —COOM (wherein $M^+$ is a monovalent cation or a fraction of a polyvalent cation, for example an ammonium or substituted ammonium ion or a metal ion, for example an alkali metal or alkaline earth metal ion). Particularly preferably, $M^+$ is a cation deriving from an organic base, for example meglumine.

It is also particularly preferred that the number of the ion-forming groups X in the compounds of formula I be chosen to equal the valency of the metal species to be chelated by the compound formula I. Thus, for example, where Gd(III) is to be chelated, the chelating agent of formula I preferably contains three ion-forming X groups, for example —COOH or —COOM. In this way, the metal chelate will be formed as a neutral species, a form preferred since the osmotic pressures in concentrated solutions of such compounds are low and since their toxicities relative to their ionic analogues are significantly reduced.

Compounds of formula I in which all the carboxyl or carboxyl derivative X groups are —COOH or —COOM groups are especially preferred since compositions containing such metal chelates can readily be sterilized, for example by autoclaving.

Included amongst the particularly preferred chelating agents of formula I are the compounds of formulae Ib, Ic, Id, Ie and If:

$$(XR_1HC)_2N-(CHR_1)_2-N(CHR_1X)_2 \quad \text{(Ib)}$$

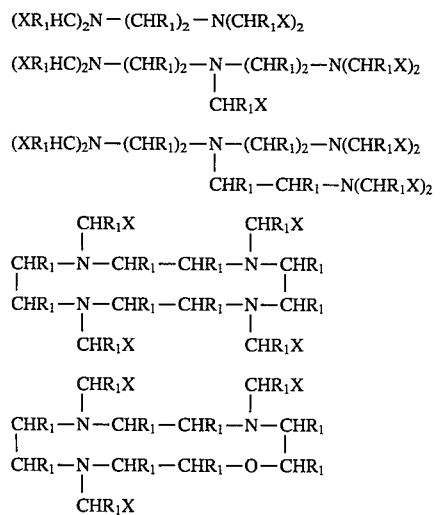

(wherein at least 2, and preferably 3 or 4, of the X groups are ion-forming groups (for example —COOH or —COOM groups), preferably wherein at least one and especially preferably at least two $R_1$ groups are hydrophilic groups, and particularly preferably wherein at least one $R_1$ group in each —$(CHR_1)_2$ moiety is a hydrophilic $R_1$ group).

Preferred compounds of formula I include certain compounds of formulae Ib to If wherein each moiety —$CHR_1X$ is of formula —$CH_2X''$ wherein $X''$ is a carboxyl group or a derivative thereof.

Viewed from a further aspect, the invention provides a process for the preparation of the compounds of formula I, said process comprising one or more of the following steps:

(i) reacting a corresponding amine to introduce a —$CHR_1X$ moiety at an amine nitrogen;

(ii) converting a carboxyl X moiety in a compound of formula I into a carboxyl derivative thereof or a carboxyl derivative X moiety in a compound of formula I into a carboxyl group; and (iii) converting a compound of formula I into a salt or metal chelate thereof or converting a salt or chelate of a compound of formula I into a compound of formula I.

Process step (i) may conveniently be performed by reacting a compound essentially of formula I but having at least one hydrogen atom in place of a —$CHR_1X$ moiety and optionally having in place of X and/or $R_1$ moieties groups convertible thereto (for example groups convertible by the removal of protecting groups), with a compound of formula IV $$R_2\ CHR_1'X' \quad \text{(IV)}$$

(wherein $R_2$ is a leaving group, for example a nucleophilically displaceable group such as a halogen atom, preferably a bromine atom; and $R_1'$ and $X'$, which are not both hydrogen atoms, are as defined for $R_1$ and X or are groups convertible thereto, for example by deprotection).

As protecting groups, conventional protecting groups may be used, for example groups such as are described by T. W. Greene in "Protective Groups in Organic Synthesis", John Wiley & Sons, 1981 For the protection of hydroxyl groups, particular mention may be made however of the utility of benzyl protecting groups which are stable over a wide pH range but are readily removed by hydrogenolysis as described by T. W. Greene. Polyhydroxyalkyl groups may for example alternatively be protected in the form of cyclic polyether groups, for example as 2,2-dimethyl-1,3-dioxacyclopent-4-yl groups, as such cyclic polyether groups can be opened by acid hydrolysis to leave the unprotected polyhydroxyalkyl group.

Thus for example, introduction of a —$CHR_1X$ moiety may be effected by reacting an amine of formula II

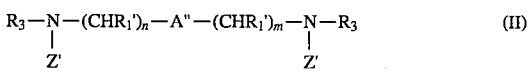

(wherein $R_3$ is a hydrogen atom or a —$CHR_1'X'$ group; $X'$ and $R_1'$ are as defined above; each group $Z'$ is a group —$CHR_1'X'$ or an $R_3$ moiety or together the groups $Z'$ are a —$(CHR_1')_q$—$A'''$—$(CHR_1')_r$— bridging group where $A'''$ is an oxygen or sulphur atom or a group

where $Y'$ is an $R_3$ moiety or a group —$(CHR_1')_p$—$N(R_3)_2$; and $A''$ is a group

or —A"—(CHR$_1$')$_m$— is a carbon-nitrogen bond or, where the groups Z' together form a bridging group, A" may also represent an oxygen or sulphur atom; with the provisos that at least one R$_3$ moiety is a hydrogen atom, that at least two amine nitrogens carry a hydrogen atom or a —CHR$_1$'X' moiety in which X' is or is convertible to a carboxyl group or a derivative thereof, and that each —CHR$_1$'X' moiety is other than a methyl group) with a compound of formula III (as defined above), followed if required by converting R$_1$' or X' to R$_1$ or X.

The process of step (i) is particularly preferably effected by reacting a compound of formula II (in which any hydroxyl moieties are protected) with bromoacetic acid or a derivative thereof, for example the sodium salt or an ester, followed by deprotection of the hydroxyl moieties.

To introduce —CHR$_1$X groups wherein R$_1$ is hydroxy or hydroxyalkyl, alternative compounds of formula III, such as 3-bromo-oxacyclopentan-2-one, Hal.CH$_2$CH$_2$OH, Hal CH$_2$CHOHCH$_2$OH or R$_5$—OCH$_2$—CHHal—COOH (wherein Hal is a halogen atom such as a bromine atom and R$_5$ is a protecting group) may of course be used.

Thus for the process of step (i) the following preferred starting compounds of II may be used:

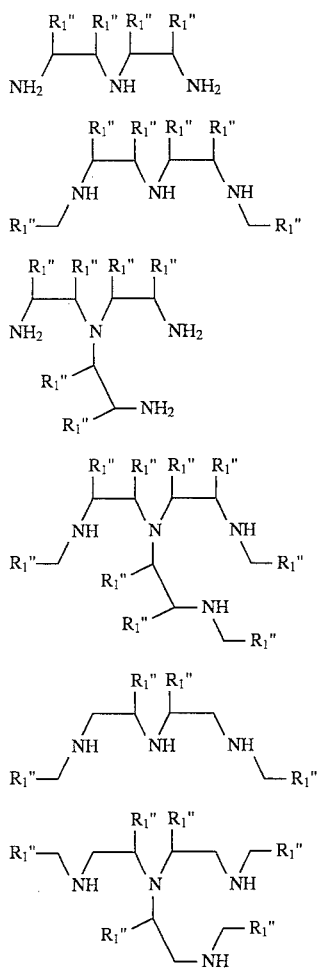

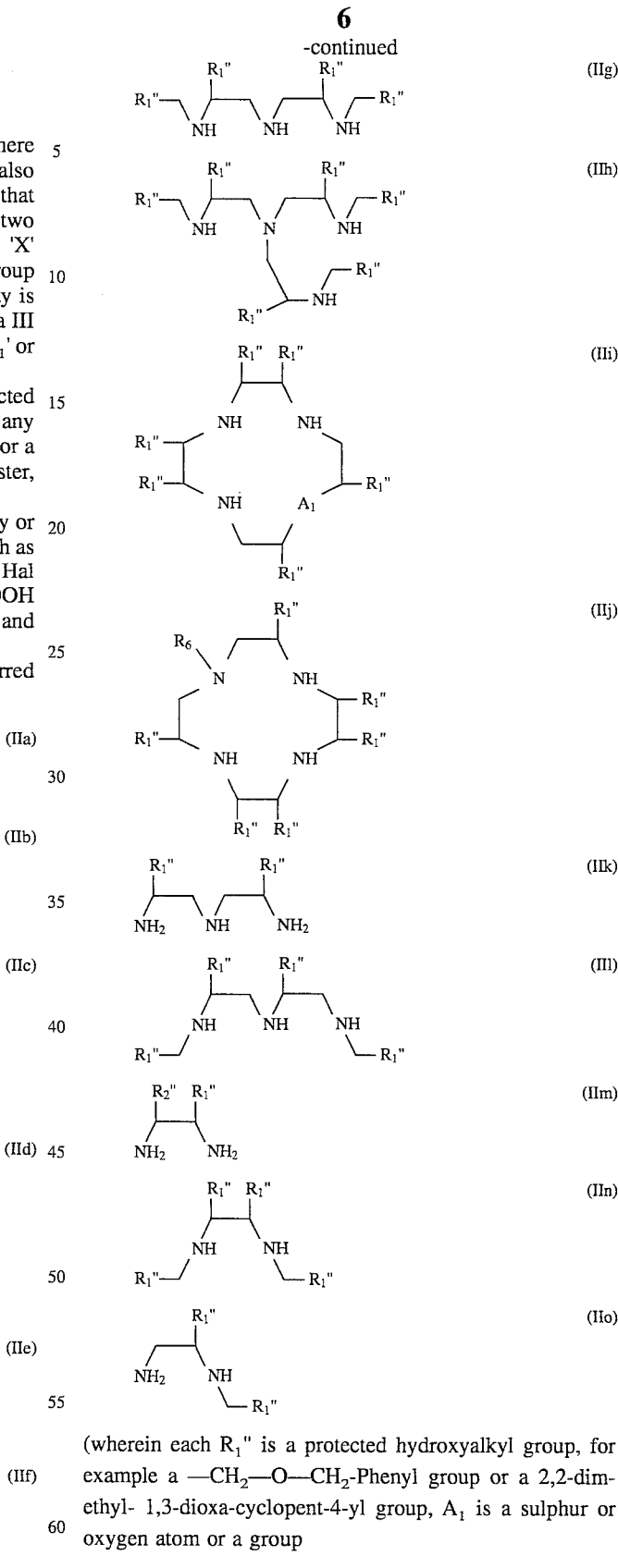

(wherein each R$_1$" is a protected hydroxyalkyl group, for example a —CH$_2$—O—CH$_2$-Phenyl group or a 2,2-dimethyl-1,3-dioxa-cyclopent-4-yl group, A$_1$ is a sulphur or oxygen atom or a group

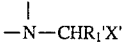

(for example a

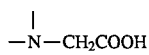

group) and $R_6$ is a group —CHR$_1$'X' or a moiety convertible thereto). In the starting compounds of formulae IIa to IIo, protected hydroxyalkyl groups attached to the alkylene chains between amine nitrogens are preferably benzyl protected groups and the nitrogen-attached protected hydroxyalkyl groups in —CHR$_1$'X' moieties are preferably in the form of cyclic polyethers.

The preparation of starting compounds of formulae IIa to IIo, which compounds themselves form further aspects of the present invention, may for example be by the following procedures:

Compounds of formula IIa may be prepared by the following scheme.

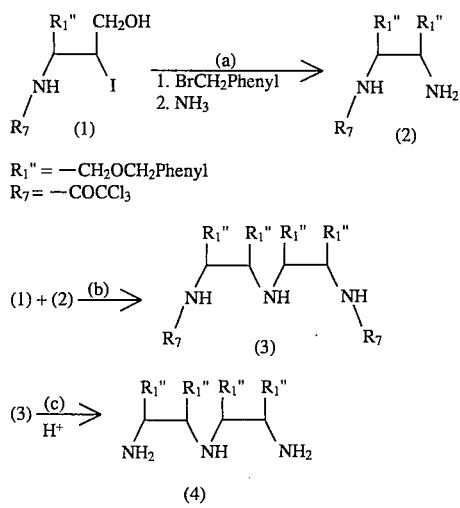

The starting compound (1) is described by A. Bongini et al. in J. Chem. Soc., Perkin Trans. 1, (1985) 935. It can be converted by benzyl protection of the remaining alcohol group and by ammonolysis to compound (2) and then condensation of compounds (1) and (2) and subsequent acid hydrolysis can yield compound (4) which is of formula IIa.

Compounds of formula IIb may be prepared from compounds of formula IIa by reductive amination, for example as described by R. F. Borch in J. Org. Chem. 34 (1969) 627, using a protected aldehyde prepared for example as described by C. Hubschwerlen in Synthesis (1986) 962. The reaction may for example follow the scheme:

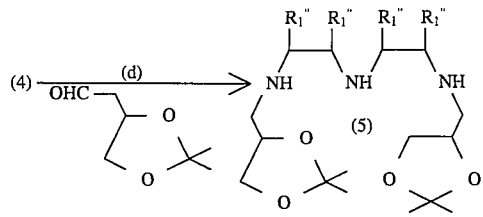

Compounds of formulae IIm and IIn may be prepared analogously to compounds of formulae IIa and IIb by omitting the condensation step (b) in the above scheme.

Compounds of formula IIc may be prepared analogously to compounds of formula IIa by condensation of compounds (1) and (2) and subsequent acid hydrolysis, for example according to the scheme:

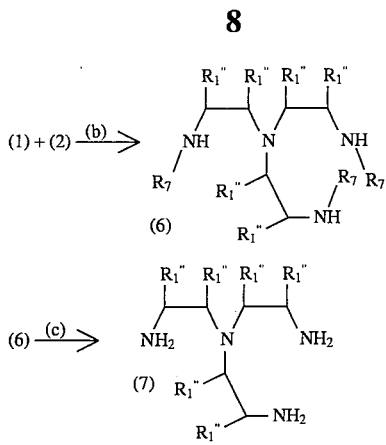

Compounds of formula IId may be prepared analogously to compounds of formula IIb by reductive amination of compounds of formula IIc, for example following the scheme:

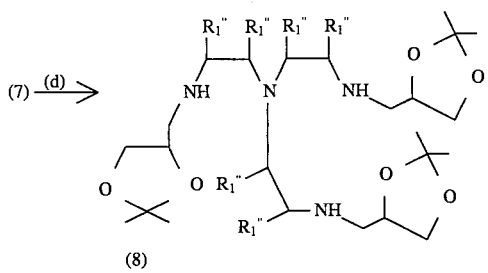

Compounds of formula IIe may be prepared by the following scheme:

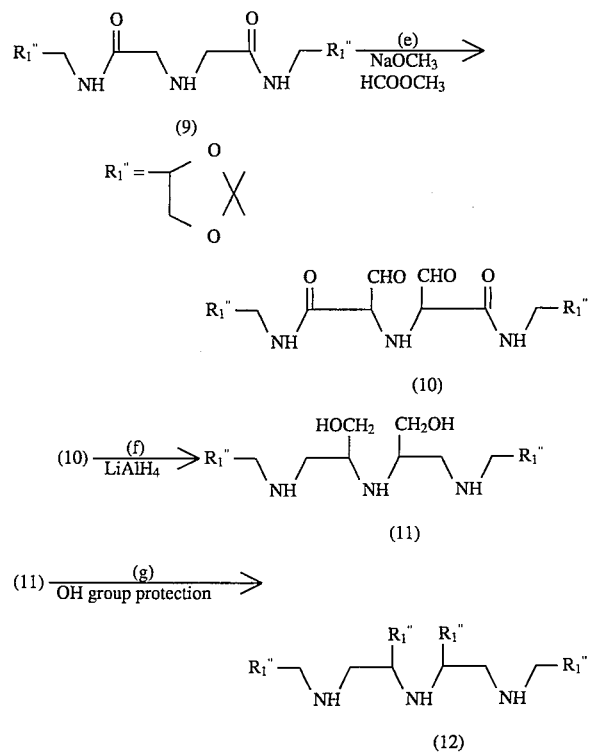

Compounds of formula IIf may be prepared analogously to compounds of formula IIe using a triamide starting material:

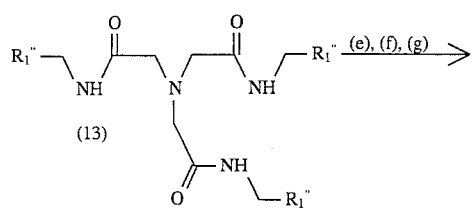

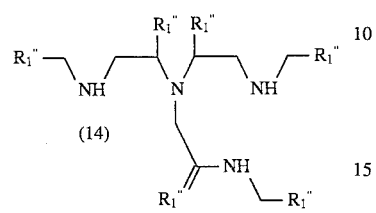

The α-formylation described above may be performed using the method described in J. Med. Chem. 8 (1965) 220.

Alternatively, compounds of formulae IIe and IIf may be prepared by replacing the formylation step (e) by reaction with chloromethylbenzylalcohol (available from Fluka) to yield the starting compounds (15) and (16) for the reduction step (f):

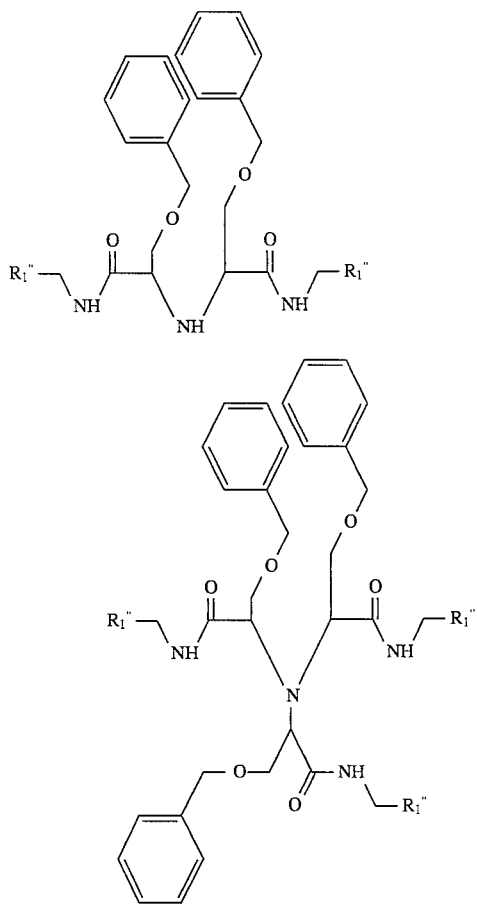

The direct insertion of benzyl-protected hydroxymethyl groups may be performed as described in Org. Syn. 52 (1972) 16.

Compounds of formula IIg may be prepared by the following scheme:

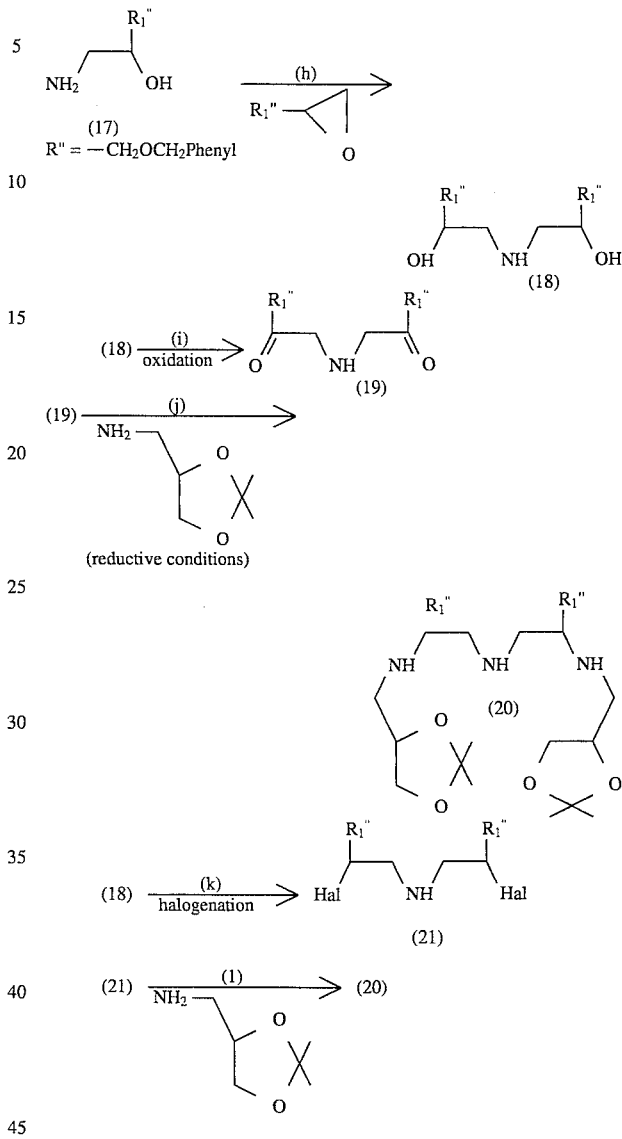

Compounds of formula (17) may be produced by mono-protection of aminopropandiol at the primary hydroxyl group and may be mono or di-alkylated using a glycidol ether. The mono and di-alkylation products may be separated by distillation. The mono-alkylation product, compound (18), is used in the preparation of compounds of formula IIg and the dialkylation product, compound (22) below, may be used in the preparation of compounds of formula IIh. The mono-alkylated compound (18) may be converted to compound (20), which is of formula IIg, by oxidation and subsequent reductive amination or by halogenation and subsequent amination.

Compounds of formula IIh may be prepared analogously to the compounds of formula IIg, for example according to the scheme:

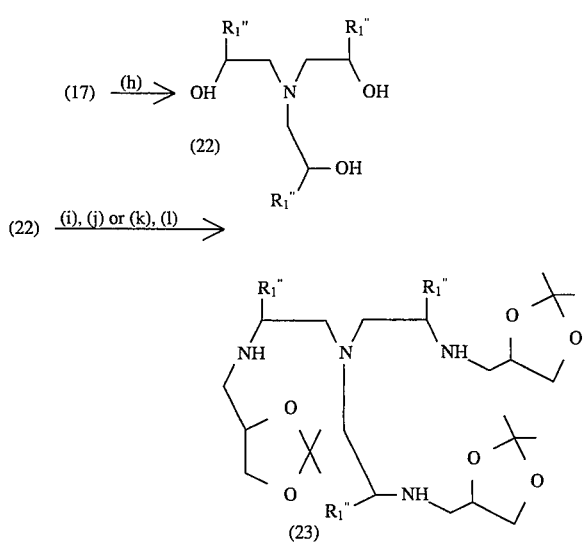

Compounds of formula IIo can be prepared analogously to compounds of formula IIg by omitting the initial mono-/di-alkylation step (h).

The cyclic compounds of formula IIi may be prepared by peptide condensation followed by reduction of the amide carbonyl groups, substantially as described by J. Tabushi et al. in Tetr. Lett. (1976) 4339 and (1977) 1049. The reaction may be performed according to the following scheme:

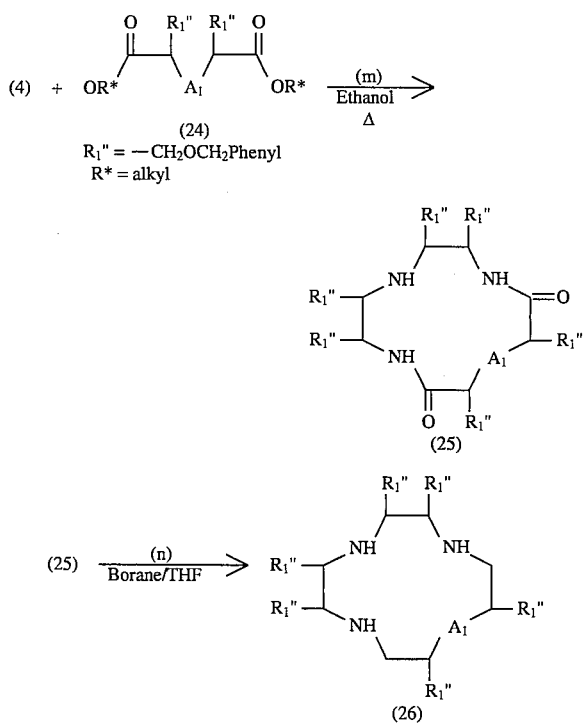

The starting compound (24), wherein $A_1$ is an amine group, may be prepared by alkylation of an iminodiacetic acid derivative and the ether and thioether starting compounds may be prepared analogously by formylation of the corresponding starting materials, for example as described by W. Rasshofer et al. in Chem. Bet. 112 (1979) 2095. Compounds of formula IIi are particularly preferred starting materials as they may be used to form non-ionic or mono-ionic chelates with trivalent metal ions according to the selection of $A_1$.

The cyclic compounds of formula IIj may be prepared by the well known routes for the preparation of cyclic polyamines. Thus, in a method analogous to that described by J. E. Richmann et al. in J. Am. Chem. Soc. 96 (1974) 2268, compounds of formula IIa may be tosylated and the resultant product may then be cyclized with a di(protected hydroxyalkyl) amine, which may itself be prepared from compound (18). Thus the compounds of formula IIj may for example be prepared by the following scheme:

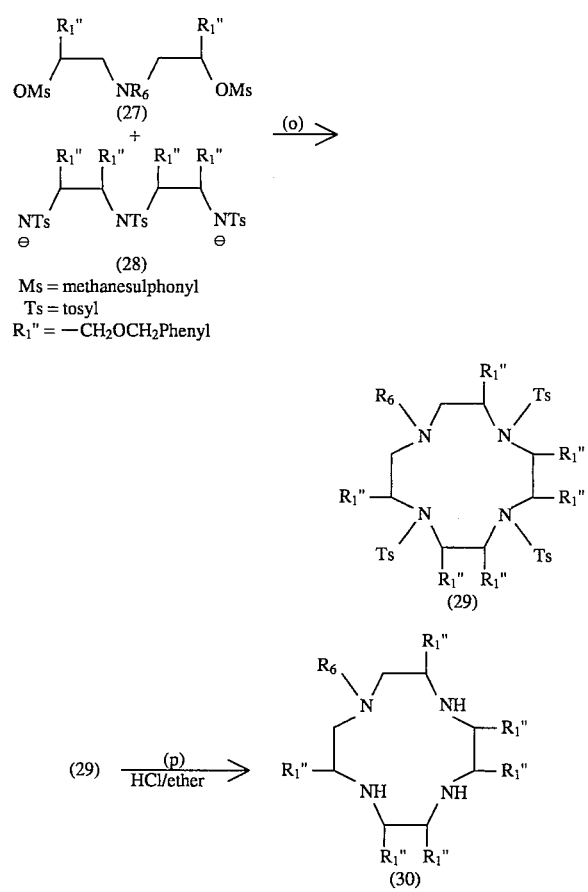

Compound (27) may be prepared from compound (18) by a method analogous to that described by M. Hediger et al. in J. Chem. Soc, Chem Commun (1978) 14 and by J. Pless et .al. in Chem. Abs 71 (1969) 49569x. Various detosylation methods for step (p) are known, as described for example by W. Rasshofer et al. in Liebigs Ann Chem. (1977) 1344. The group $R_6$ may be a protecting group resistant to the detosylation conditions allowing the possibility of substituting the nitrogen to which it is attached with a carboxymethyl derivative, etc.

Compounds of formula IIk may be prepared by a reaction scheme substantially as follows:

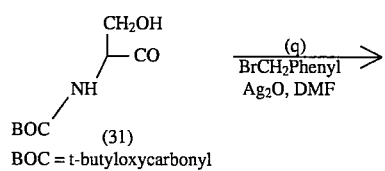

BOC = t-butyloxycarbonyl

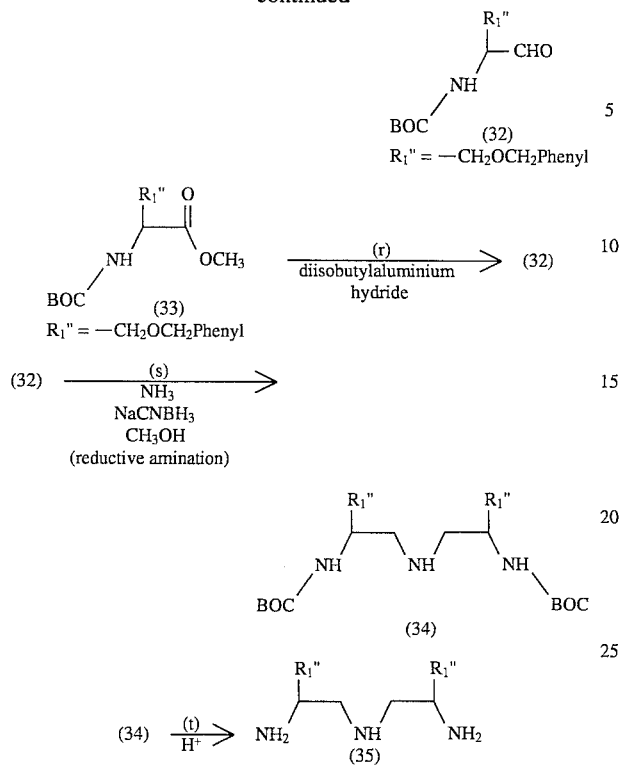

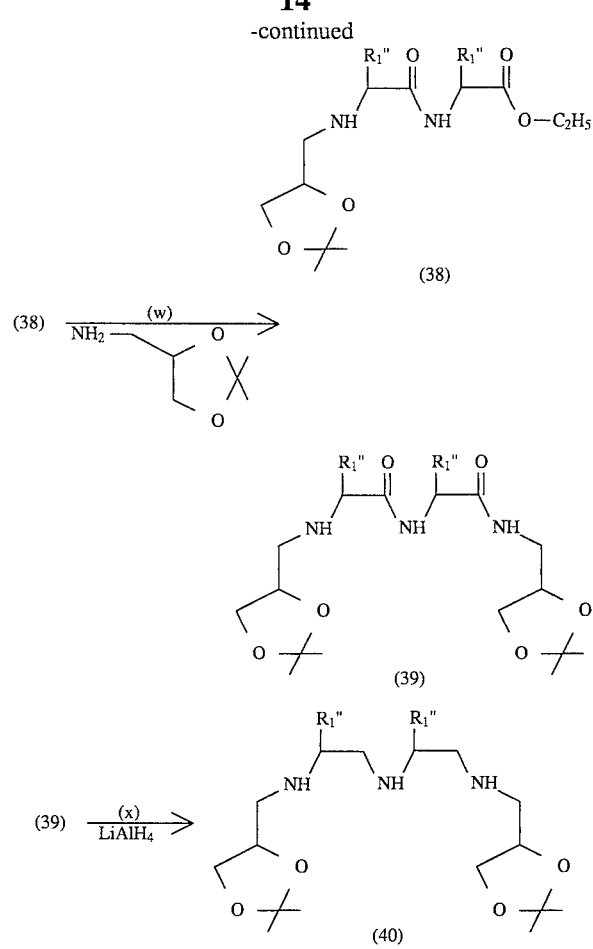

The starting compound (31) is described by Y. Ohfune et al. in Tetr. Lett. (1984) 1071. Protection of the alcohol function as a benzyl ether gives compound (32) which alternatively can be obtained by reducing the commercially available serine ester, compound (33), as described in Chem. Pharm. Bull. 23 (1975) 3081. Reductive amination of compound (32) yields compound (34) from which the BOC (t-butyloxycarbonyl) groups may be removed by acid hydrolysis to yield compound (35) which is of formula IIk. Compounds of formula IIg may be prepared by alkylation of compounds of formula IIk, for example with 2-(2,2-dimethyl-1,3-dioxa-cyclopent- 4-yl)-ethylamine. This reaction would generally be performed as a reductive amination. The asymmetric compounds of formula III may be prepared by peptide condensation of protected amino acids followed reduction of the amide carbonyl groups, for example using the following scheme:

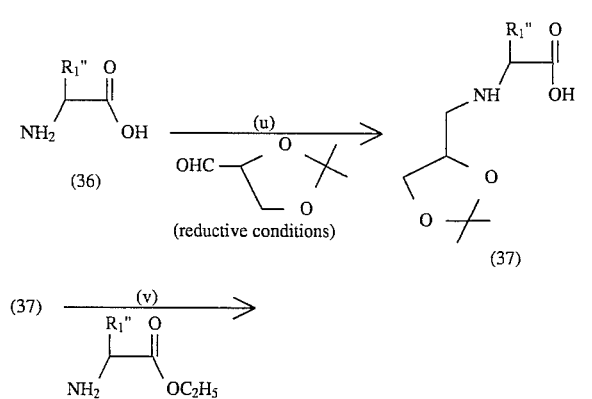

Reductive amination of O-benzyl serine with glyceraldehyde acetal gives compound (37) and coupling of compound (37) with the ethyl ester of O-benzyl protected serine gives the dipeptide compound (38) (see J. Martinez et al. Int. J. Peptide Protein Res.12 (1978) 277). Amidation of compound (38) with a protected amino alcohol gives compound (39) which may be reduced to compound (40) using lithium aluminium hydride, as described by J. E. Nordlander et al. in J. Org. Chem. 49 (1984) 133. Compound (40) is a compound of formula III. If the amidation step (w) is omitted, reduction of compound (38) will give further asymmetric compounds of formula II.

Reaction of starting compounds of formula IIa to IIo with sodium bromoacetate and subsequent deprotection of the protected groups by acid hydrolysis or by hydrogenolysis will yield corresponding compounds of formulae IA to IO:

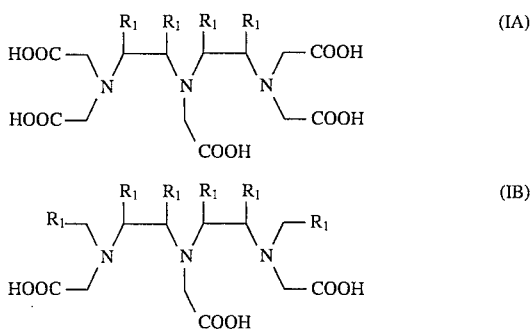

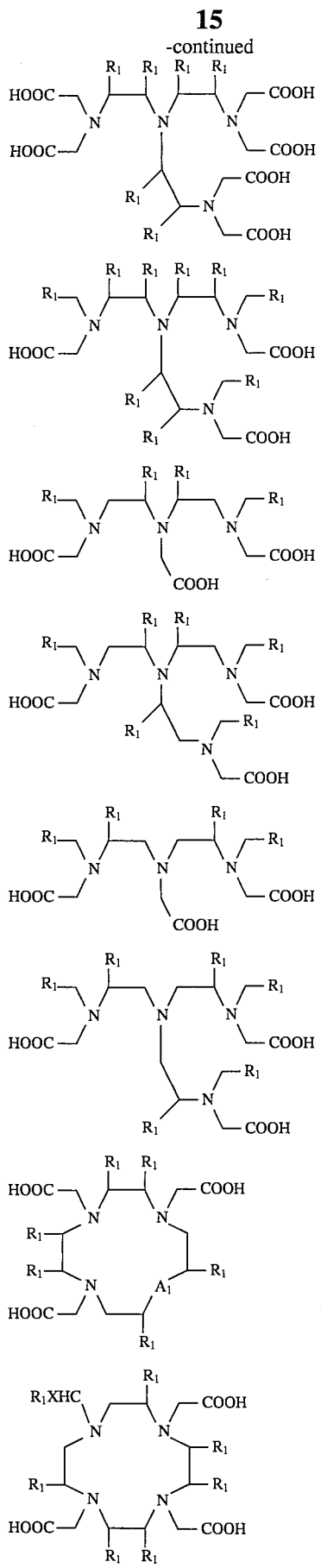
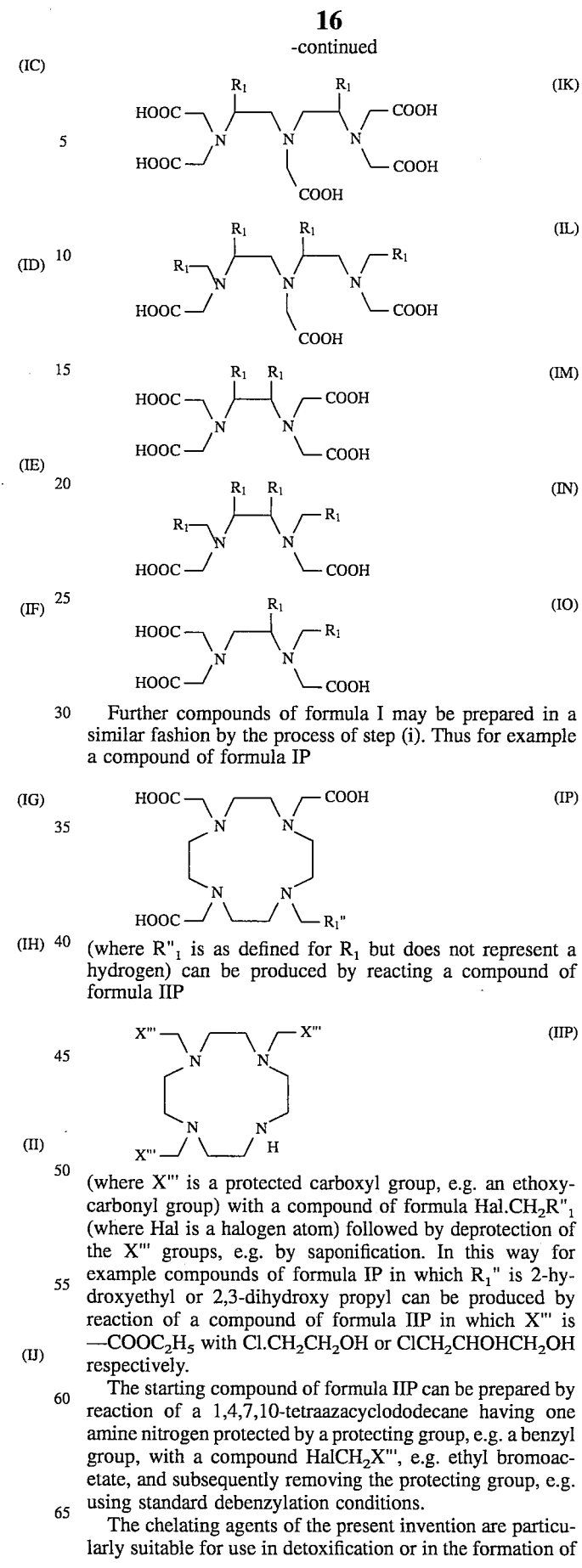

Further compounds of formula I may be prepared in a similar fashion by the process of step (i). Thus for example a compound of formula IP (where R"$_1$ is as defined for R$_1$ but does not represent a hydrogen) can be produced by reacting a compound of formula IIP (where X''' is a protected carboxyl group, e.g. an ethoxycarbonyl group) with a compound of formula Hal.CH$_2$R"$_1$ (where Hal is a halogen atom) followed by deprotection of the X''' groups, e.g. by saponification. In this way for example compounds of formula IP in which R$_1$" is 2-hydroxyethyl or 2,3-dihydroxy propyl can be produced by reaction of a compound of formula IIP in which X''' is —COOC$_2$H$_5$ with Cl.CH$_2$CH$_2$OH or ClCH$_2$CHOHCH$_2$OH respectively.

The starting compound of formula IIP can be prepared by reaction of a 1,4,7,10-tetraazacyclododecane having one amine nitrogen protected by a protecting group, e.g. a benzyl group, with a compound HalCH$_2$X''', e.g. ethyl bromoacetate, and subsequently removing the protecting group, e.g. using standard debenzylation conditions.

The chelating agents of the present invention are particularly suitable for use in detoxification or in the formation of metal chelates, chelates which may be used for example in or as contrast agents for in vivo or in vitro magnetic resonance (MR), X-ray or ultrasound diagnostics (e.g. MR imaging and MR spectroscopy), or scintigraphy or in or as therapeutic agents for radiotherapy, and such metal chelates form a further aspect of the present invention.

For use as an MR-diagnostics contrast agent, the chelated metal species is particularly suitably a paramagnetic species, the metal conveniently being a transition metal or a lanthanide, preferably having an atomic number of 21–29, 42, 44 or 57–71. Metal chelates in which the metal species is Eu, Gd, Dy, Ho, Cr, Mn or Fe are especially preferred and $Gd^{3+}$ and $Mn^{2+}$ are particularly preferred. For such use, the paramagnetic metal species is conveniently non-radioactive as radioactivity is a characteristic which is neither required nor desirable for MR-diagnostics contrast agents. For use as X-ray or ultrasound contrast agents, the chelated metal species is preferably a heavy metal species, for example a non-radioactive metal with an atomic number greater than 37.

For use in scintigraphy and radiotherapy, the chelated metal species must of course be radioactive and any conventional complexable radioactive metal isotope, such as $^{99m}Tc$ or $^{111}In$ for example, may be used. For radiography, the chelating agent may be in the form of a metal chelate with for example $^{67}Cu$.

For use in detoxification of heavy metals, the chelating agent must be in salt form with a physiologically acceptable counterion, e.g. sodium, calcium, ammonium, zinc or meglumine, e.g. as the sodium salt of the chelate of the compound of formula I with zinc or calcium.

Where the metal chelate carries an overall charge, such as is the case with the prior art Gd DTPA, it will conveniently be used in the form of a salt with a physiologically acceptable counterion, for example an ammonium, substituted ammonium, alkali metal or alkaline earth metal cation or an anion deriving from an inorganic or organic acid. In this regard, meglumine salts are particularly preferred.

Viewed from a further aspect, the present invention provides a diagnostic or therapeutic agent comprising a metal chelate, whereof the chelating entity is the residue of a compound according to the present invention, together with at least one pharmaceutical or veterinary carrier or excipient, or adapted for formulation therewith or for inclusion in a pharmaceutical formulation for human or veterinary use.

Viewed from another aspect, the present invention provides a detoxification agent comprising a chelating agent according to the invention in the form of salt with a physiologically acceptable counterion, together with at least one pharmaceutical or veterinary carrier or excipient, or adapted for formulation therewith or for inclusion in a pharmaceutical formulation for human or veterinary use.

The diagnostic and therapeutic agents of the present invention may be formulated with conventional pharmaceutical or veterinary formulation aids, for example stablizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc; however, solutions, suspensions and dispersions in physiologically acceptable carrier media, for example water for injections, will generally be preferred.

Where the agent is formulated for parenteral administration, the carrier medium incorporating the chelate or the chelating agent salt is preferably isotonic or somewhat hypertonic.

For MR-diagnostic examination, the diagnostic agent of the present invention, if in solution, suspension or dispersion form, will generally contain the metal chelate at concentration in the range 1 micromole to 1.5 mole per liter, preferably 0.1 to 700 mM. The diagnostic agent may however be supplied in a more concentrated form for dilution prior to administration. The diagnostic agent of the invention may conveniently be administered in amounts of from $10^{-4}$ to 1 mmol of the metal species per kilogram of body weight.

For X-ray examination, the dose of the contrast agent should generally be higher and for scintigraphic examination the dose should generally be lower than for MR examination. For radiotherapy and detoxification, conventional dosages may be used.

Viewed from a further aspect, the present invention provides a method of generating enhanced images of the human or non-human animal body, which method comprises administering to said body a diagnostic agent according to the present invention and generating an X-ray, MR-diagnostics, ultrasound or scintigraphic image of at least a part thereof.

Viewed from a further aspect, the present invention provides a method of radiotherapy practised on the human or non-human animal body, which method comprises administering to said body a chelate of a radioactive metal species with a chelating agent according to the invention.

Viewed from a further aspect, the present invention provides a method of heavy metal detoxification practised on the human or non-human animal body, which method comprises administering to said body a chelating agent according to the invention in the form of a salt with a physiologically acceptable counterion.

Viewed from a yet further aspect, the present invention also provides the use of the compounds, especially the metal chelates, according to the invention for the manufacture of diagnostic or therapeutic agents for use in methods of image generation, detoxification or radiotherapy practised on the human or non-human animal body.

Viewed from a still further aspect, the present invention provides a process for the preparation of the metal chelates of the invention which process comprises admixing in a solvent a compound of formula I or a salt (e.g. the sodium salt) or chelate thereof together with an at least sparingly soluble compound of said metal, for example a chloride, oxide or carbonate.

Viewed from a yet still further aspect, the present invention provides a process for the preparation of the diagnostic or therapeutic agent of the present invention, which comprises admixing a metal chelate according to the invention, or a physiologically acceptable salt thereof, together with at least one pharmaceutical or veterinary carrier or excipient.

Viewed from a vet still further aspect, the present invention provides a process for the preparation of the detoxification agent of the invention, which comprises admixing a chelating agent according to the invention in the form of a salt with a physiologically acceptable counterion together with at least one pharmaceutical or veterinary carrier or excipient.

The present invention will now be illustrated further by the following non-limiting Examples. All ratios and percentages given herein are by weight and all temperatures are in degrees Celsius unless otherwise indicated.

EXAMPLE 1

N-carboxymethyl-N,N-bis-((N'-carboxymethyl-N'-2,3-dihydroxypropyl)-2-aminoethyl)-amine (a) To a hot, stirred solution of 276 g (3.06 mol) of aminopropanediol was added dropwise 55.2 g (0.29 mol) of iminodiacetic acid diethyl ester (from Tokyo Kasei) dissolved in absolute ethanol (1:1 by weight). After 3 hours at 120° C. bath temperature, and evaporation of the ethanol, the excess aminopropanediol was removed by distillation at $10^{-2}$ torr. NMR and TLC analysis showed quantitative conversion to the product diamide, with an about 10% content of aminopropanediol. The product was purified by treatment with weak acidic cation exchanger IRC (Fluka) to yield 78.5 g of a yellow oil. Yield 96%.

(b) 70 g (0.25 mol) of the product diamide was dissolved in 175 ml of dry N,N-dimethylformamide (DMF) and 208 g (1.25 mol) of 1,1-dimethoxy-ethyl-benzene and 47.5 g (0.25 mol) of p-toluenesulfonic acid monohydrate was added. The solution was heated at 60° C./200 mbar in a rotary evaporator for 2.5 hours and excess dry sodium carbonate was added. Host of the solvent was evaporated and 300 ml of saturated sodium bicarbonate solution was added, after which the solution was concentrated almost to dryness. Extraction with chloroform, washing with water, drying and conventional working up yielded a yellow oil which, after 8 hours evaporation at $10^{-3}$ mbar, gave 179 g product. The product was used directly in the next step.

(c) To a solution of 46.8 g (1.23 mol) of lithium aluminium hydride in 1.5 l of freshly distilled THF covered by nitrogen, was carefully added 37.2 g (76.9 mmol) of ketal (Example 1(b)) into 200 ml of tetrahydrofuran (THF). The solution was refluxed for 4 hours and the reaction product was hydrolysed at 0° C. on an ice/water bath by 47 ml of water in THF, by 47 ml of 15% by weight NaOH and by 141 ml of water successively. After addition of 1 liter of THF, the suspension was filtered off, washed with THF and the mother liquors were evaporated to dryness to give 25.5 g (73%) of the ketal-protected triamine as a yellow oil.

(d) To the solution of 20 g (43.9 mmol) of the protected triamine in 100 ml of methanol in water (7:3 by volume) was added 28.3 g (176 mmol) of sodium bromoacetate and the pH was kept in the alkaline range for 4 hours at 40° C. Adjustment of the pH to 3.5 and cooling on an ice/water bath gave a yellowish oil which was treated with HBr solution in acetone/water at pH 1 overnight at ambient temperature. The mixture was concentrated to half its volume, washed with chloroform and treated with a strongly cationic exchanger Dowex 50Wx4. The gel was filtered off and washed with diluted ammonia. After adjustment with formic acid to pH 3.5, the solution was concentrated to dryness under high vacuum at 60° C. or by lyophilization to yield 9.3 g of a white solid. Mp 51°–55° C. Yield 50%.

EXAMPLE 2

N,N,N-Tris-((N'-carboxymethyl-N'-2,3-dihydroxypropyl)-2-aminoethyl)-amine (a) 41 g (0.21 mol) of nitrilotriacetic acid was suspended in 400 ml of dry ethanol and 22.5 g of concentrated sulphuric acid was added. The reaction mixture was refluxed for 4 hours while the solvent was constantly evaporated. The clear solution was concentrated to dryness, dissolved in chloroform, washed with saturated sodium bicarbonate and water and dried with sodium sulphate. Work-up yielded 58.7 g of a colourless oil. Yield 99.5%.

(b) To a hot, stirred solution of 164 g (1.81 mol) of aminopropanediol was added dropwise 50.0 g (0.18 mol) of the product nitrilotriacetic acid triethylester dissolved in absolute ethanol (1:1 by volume). After 3 hours at 120° bath temperature, and evaporation of the ethanol, the excess aminopropanediol was removed by distillation at $10^{-2}$ torr. NMR and TLC analysis showed quantitative conversion to the product diamide, with an about 10% content of aminopropanediol. The product was purified by treatment with weak acidic cation exchanger IRC (Fluka) to yield 73.5 g of a yellow oil. Yield 99.5%.

(c) 25.0 g (61 mmol) of the product amide was dissolved in dry DMF and 75.9 g (0.460 mol) of 1,1-dimethoxy-ethyl-benzene and 5.96 g (31 mmol) of p-toluenesulfonic acid monohydrate was added. The solution was heated at 60° C./200 mbar in a rotary evaporator for 2.5 hours and excess dry sodium carbonate was added. Most of the solvent was evaporated and 125 ml of saturated sodium bicarbonate solution was added, after which the solution was concentrated almost to dryness. Extraction with chloroform, washing with water, drying and conventional working up yielded a yellow oil which, after 8 hours evaporation at $10^{-3}$ mbar, gave 37.7 g of product. The product was used directly in the next step.

(d) To a solution of 36 g (0.949 mol) of lithium aluminium hydride in 1.5 l of freshly distilled THF covered by nitrogen, was carefully added 37 g (52 mol) of ketal (Example 2(c)) into 200 ml THF. The solution was refluxed for 4 hours and the reaction product was hydrolysed at 0° C. on an ice/water bath by 36 g of water in THF, by 36 g of 15% by weight NaOH and by 108 g of water successively. After addition of one liter of THF, the suspension was filtered off, washed with THF and the mother liquors were evaporated to dryness to give 23.7 g (68%) of the ketal-protected triamine as a yellow oil.

(e) To the solution of 23 g (34 mmol) of the protected triamine in methanol-in-water (7: 3 by volume) was added 18.9 g (136 mmol) of sodium bromoacetate and the pH was kept in the alkaline range for 4 hours at 40° C.

Methanol was evaporated, and addition of 400 ml of 20% by weight sodium chloride solution gave a yellow oil. After decantation, the oil was dissolved in acetone and water (1:1 volume), the pH was adjusted to 1 with HBr and the solution was stirred overnight. The mixture was then concentrated to half its volume, washed with chloroform and treated with a strongly cationic exchanger Dowex 50Wx4. The gel was filtered off and washed with diluted ammonia. After adjustment with formic acid to pH 3.5, the solution was concentrated to dryness under high vacuum at 60° C. or by lyophilization to yield 8.3 g of a white solid. Mp 82°–86° C.

EXAMPLE 3

1-Oxa-4,7,10-triazacyclododecane-N,N',N"-triacetic acid

A solution of bromoacetic acid (2.22 g (16 mmol)) and sodium hydroxide (0.64 g (16 mmol)) in 8 ml of water was added dropwise to a solution of 1-oxa- 4,7,10-triazacyclododecane (0.80 g (4.6 mmol) ) in 5 ml of water. (The compound 1-oxa-4,7,10-triazacyclododecane was prepared according to the procedure described by W. Rasshofer, W. Wehner and F. Vögtle in Liebigs Ann. Chem., 916 (1976)).

The mixture was heated to 80° C. and, while being stirred, 4M sodium hydroxide 4 ml was added dropwise. The temperature was maintained at 80° C. for two hours and then

21 brought down to ambient temperature. The pH was adjusted to 3.4 with 6N HCl. Ethanol (250 ml) was added and a white crystalline precipitate was formed. The product was filtered off and washed with 50 ml of ethanol. The product was further purified by treatment with a cation exchange resin (Dowex 50 Wx4). Yield: 65%. M.p.: 190° C. (dec)

EXAMPLE 4

3,6-Bis-(carboxymethyl)-4-hydroxyethyl-3,6-diazaoctanediacid (a) N-triphenylmethyl-α-aminobutyrolactone α-Aminobutyrolactone hydrobromide (10.0 g, 54.9 mmol), N-methylmorpholine (11.2 g, 110.0 mmol) and triphenylmethyl chloride (15.4 g, 55.2 mmol) were dissolved in N,N-dimethylformamide (DMF) (200 ml) (distilled from calcium hydride) and stirred at ambient temperature for 16 hours. The mixture was filtered, and water (200 ml) was added to the DMF-solution. The resulting slurry was stirred for 2 hours, the precipitate was filtered off and washed with a mixture of DMF and water (1:1, 50 ml). The solid was resuspended in water (100 ml), filtered and dried at 50° C. in vacuo. N-triphenylmethyl-α-aminobutylrolcatone was isolated as a white solid. Yield 17.55 g (93.2%), mp 164.5°–165.5° C. (uncorrected).

(b) 1-Carboxamido-3-hydroxy-1-(N-triphenylmethylamino)propane

N-triphenylmethyl-α-aminobutyrolactone (4.0 g, 11.66 mmol) was dissolved in tetrahydrofuran (THF) (20 ml) in a 100 ml pressure vial. Methanol saturated with ammonia (20 ml) was added, and the sealed tube was heated to 70° C. for 48 hours with stirring. After cooling to ambient temperature the solvent was evaporated, the residue was dissolved in ether (75 ml), n-hexane (7.5 ml) was added and the solution was kept at 4° C. for 24 hours. 1-Carboxamido-3-hydroxy-1-(N-triphenylmethylamino)-propane precipitated as yellow crystals. Yield 3.0 g (71%). The structure was confirmed by $^{13}$CNMR and $^1$HNMR.

(c) 1,2-diamino-4-hydroxybutane dihydrochloride

1-Carboxamido-3-hydroxy-1-(N-triphenylmethylamino)propane (2.5 g, 6.94 mmol) was dissolved in THF (25 ml) (distilled from lithium aluminium hydride). Lithium aluminium hydride (1.9 g, 50 mmol) was added and the mixture was refluxed overnight. Aqueous THF (50 ml, 4% water), 2N NaOH (2 ml) and aqueous THF (50 ml, 4% water) were added successively dropwise at 0° C. and the mixture was stirred for 1 hour. The slurry was filtered, and the THF solution was evaporated to dryness. The resulting oil was suspended in methanol (2 ml), applied to a silica column and eluted with methanol (180 ml) and methanol: saturated aqueous ammonia 90:10 (180 ml). The last fraction was evaporated and the resulting oil (1.0 g) was dissolved in acidic methanol (25 ml containing 2 ml 12N hydrochloric acid). After 12 hours the solvent was evaporated and 1,2-diamino-4-hydroxybutane dihydrochloride was isolated as a white solid. Yield 0.49 g (42%), FAB MS: 105(M+1). The structure was confirmed by $^1$HNMR and $^{13}$CNMR.

22

(d) 3,6-Bis-(carboxymethyl)-4-hydroxyethyl-3,6-diazaoctanediacid 1,2-Diamino-4-hydroxybutane (0.35 g, 3.36 mmol) was dissolved in water (10 ml), and pH was adjusted to 9.5 with lithium hydroxide. Bromoacetic acid lithium salt (1.38 g) was added and the mixture was heated to 50° C. and stirred at this temperature for 24 hours. During this period pH was kept constant (9–10) by adding a solution of lithium hydroxide (1M). The mixture was cooled to ambient temperature and applied to a Biorad AG 50W-X4 column (80 ml) and eluted with water and aqueous saturated ammonia. The title compound was isolated as a yellow solid. Yield 0.45 g (61%), mp greater than 350° C. FAB MS: 337(M+1). The structure was confirmed by $^1$HNMR and $^{13}$CNMR.

EXAMPLE 5

1-Thia-4,7,10-triazacyclododecane triacetic acid (a) Thiodiglycolicacid dimethyl ester Thiodiglycolic acid (150.2 g, 1.0 mol) was dissolved in methanol (244 ml) and 1,2 dichloroethane (300 ml). KSF-catalyst (Aldrich) (5 g) was added and the mixture was refluxed for 14 hours. The mixture was cooled to ambient temperature and was filtered through alumina. The organic phase was separated and concentrated. Thiodiglycolicacid dimethyl ester was isolated as a yellow oil after high vacuum distillation. Yield 100 g (56%), b.p. 82°–100° C. (0.01 mm Hg). The structure was confirmed by $^1$HNMR and $^{13}$CNMR.

(b) 1-Thia-4,7,10-triazacyclododecane-3,11-dione

Diethylene triamine (9.3 g, 90 mmol) and thiodiglycolicacid dimethyl ester (16.2 g, 90 mmol) were dissolved in methanol (1800 ml). The mixture was refluxed for 96 hours followed by concentration to 100 ml. The precipitate was isolated by filtration, washed with methanol (10 ml) and dried. 1-Thia-4,7,10-triazacyclododecane- 3,11-dione was isolated as a white solid. Yield 2.6 g (13.5%) mp 206°–208° C. (uncorrected). The structure was confirmed by $^1$HNMR and $^{13}$CNMR.

(c) 1-Thia-4,7,10-triazacyclododecane

1-Thia-4,7,10-triazacyclododecane-3,11-dione (8.10 g, 37.3 mmol) was suspended in dry THF (distilled from lithium aluminium hydride) (2000 ml) and refluxed under nitrogen for 8 hours with continuous addition of freshly generated diborane (approx. 0.4 mol in total). The reaction mixture was cooled to ambient temperature, 6N HCl (80 ml) was added, and the mixture was stirred for 1 hour. Sodium hydroxide (20 g, 0.5 mol) was added and the solution was evaporated to dryness. The residue was extracted with ethanol (3×50 ml), the extracts were concentrated and 1-thia-4,7,10-triazacyclododecane was purified by extraction (acetonitrile) and sublimation (Kugelrohr). Yield 3.73 g (53%), white solid, m.p. 51°–54° C. (uncorrected). The structure was confirmed by $^1$HNMR and $^{13}$CNMR.

(d) 1-Thia-4,7,10-triazacyclododecane triacetic acid

1-Thia-4,7,10-triazacyclododecane (0.378 g, 2 mmol) was dissolved in methanol (20 ml). Bromoacetic acid (1.04 g, 7.5 mmol) was dissolved in water by adjusting the pH to 10 with lithium hydroxide (4M) and this aqueous solution was added to the methanol solution. The mixture was stirred at 40° C. for 6 hours by repeated adjustment of pH to 9–10 with lithium hydroxide. The mixture was concentrated in vacuo, the residue was dissolved in water (5 ml) and purified on an AG 50W-X4 cation exchanger. The concentrated eluate was recrystallised from methanol/2-propanol. The title compound was isolated as a white powder. Yield 0.422 g (48%) m.p. 113°–117° C. The structure was confirmed by $^1$HNMR and $^{13}$CNMR.

EXAMPLE 6

$N^3,N^6,N^9$-Tris-carboxymethyl-4,8-bis-hydroxymethyl-3,6,9-triazaundecanediacid (a) N-Boc-O-benzylserine methyl ester N-Boc-O-benzylserine-hydroxysuccinimide (16.0 g, 40.8 mmol) was dissolved in methanol (300 ml) and stirred at 50° C. for 24 hours. The solvent was evaporated and the residue was taken up in ethyl acetate (120 ml), washed with aqueous saturated sodium bicarbonate (2×50 ml) and water (50 ml). The organic solution was dried with sodium sulphate and after evaporation of the solvent the N-Boc-O-benzylserine methyl ester was isolated as a colourless oil. Yield 9.9 g (83%). The structure was confirmed by $^1$HNMR and $^{13}$CNMR.

(b) N-Boc-O-benzylserinal

N-Boc-O-benzylserine methyl ester (9.5 g, 32 mmol) was dissolved in dry toluene (distilled from sodium) (100 ml). The solution was cooled to −70° C., and a solution of diisobutylaluminium hydride in toluene (1.2M, 53 ml, 64 mmol) was added dropwise over a period of 45 minutes under vigorous stirring under nitrogen. The mixture was stirred for an additional 20 minutes and was then allowed to reach −50° C. Hydrochloric acid (2M, 150 ml) was carefully added and the resulting reaction mixture was allowed to reach −10° C. The organic layer was separated and the aqueous layer was extracted with ethylacetate (2×100 ml). The combined organic solution was dried with sodium sulphate and evaporated to dryness below 40° C. (bath temperature). The N-Boc-O-benzylserinal was isolated as a colourless oil. Yield 8.6 g (96%). The structure was confirmed by $^1$HNMR and $^{13}$CNMR.

(c) N,N''-di-BOC-1,5-diamino-1,5-dibenzyloxymethyl-3-aza-pentane

N-Boc-O-benzylserinal (4.0 g, 14.3 mmol), ammonium acetate (11.4 g, 144 mmol) and sodium cyanoborohydride (0.65 g, 9.3 mmol) were stirred for 16 hours at 25° C. in dry methanol (40 ml). Water (40 ml) was added and the mixture was extracted with dichloromethane (2×100 ml). The combined extracts were dried over sodium sulphate and evaporated in vacuo. N,N''-di-BOC-1,5-diamino-1,5-dibenzyloxymethyl-3-aza-pentane was isolated as a colourless oil. Yield 3.0 g (77%). FAB MS: 544(M+1). The structure was confirmed by $^1$H NMR and $^{13}$C NMR.

(d) 1,5-Diamino-1,5-dibenzyloxymethyl-3-aza-pentane

N,N''-di-Boc-1,5-diamino-1,5-dibenzyloxymethyl-3-azapentane (3.0 g, 5.5 mmol) was dissolved in dichloromethane (8.8 ml). Trifluoroacetic acid (4.4 ml) was added and the mixture was stirred for 16 hours at 25° C. The solvent and trifluoroacetic acid were removed in vacuo. The 1,5-diamino-1,5-dibenzyloxymethyl- 3-azapentane was isolated as a colourless oil. Yield 2.9 g (99%). The structure was confirmed by $^1$H NMR and $^{13}$C NMR.

(e) $N^3,N^6,N^9$-Tris-carboxymethyl-4,8-bis-hydroxymethyl-3,6,9-triazaundecanediacid 1,5-Diamino-1,5-dibenzyloxymethyl-3-azapentane (5.0 g, 14.6 mmol) in methanol (20 ml) was added to a stirred solution of bromoacetic acid (12.1 g, 87.3 mmol) and lithium hydroxide (3.7 g, 87.3 mmol) in water (20 ml). The temperature was gradually increased to 85° C. during one hour and the mixture was kept stirring at 85° C. for 4 hours. The reaction mixture was kept in the alkaline range during the alkylation. The mixture was then neutralised with concentrated hydrobromic acid and was loaded on a strongly cationic exchanger (AG 50WX4) and eluted with aqueous ammonia (6M) containing ammonium formate (25 mM). The crude product was dissolved in methanol (50 ml) and 10% Palladium on carbon (3 g) was added. The mixture was kept at 50° C. overnight, filtered and evaporated. The title compound was isolated as a white powder. Yield 2.3 g (34%). m.p. greater than 350° C. FAB MS: 454(M+1). The structure was confirmed by $^1$H NMR and $^{13}$C NMR.

EXAMPLE 7

$N^4,N^7,N^{10}$-Triscarboxymethyl-1,13-bishydroxy-5,9-bis-hydroxymethyl-4,7,10-triazatridecane (a) 2-(2-Hydroxyethyl)-1,3-dioxolane Dowex MSA-1 (90 g, carbonate form) and 2-(2-bromoethyl)- 1,3-dioxolane (18.1 g, 100 mmol) were refluxed in benzene (250 ml) for 5 hours. The resin was filtered off, washed with dichloromethane (200 ml) and methanol (500 ml). The organic solvents were evaporated and the 2-(2-hydroxyethyl)-1,3-dioxolane distilled as a colourless oil. Yield 7.5 g (64%). B.p. 150° C. (80 mm Hg). The structure was confirmed by $^1$H NMR and $^{13}$C NMR.

(b) 2-(2-Benzyloxyethyl)-1,3-dioxolane 2-(2-Hydroxyethyl)-1,3-dioxolane (7.0 g, 58.3 mmol) was dissolved in dried tetrahydrofuran (distilled from sodium) (200 ml). Sodium hydride (2.0 g, 66.7 mmol, 80%) was added and the mixture was stirred at ambient temperature until gas evolution was completed. Tetrabutylammonium iodide (0.22 g, 0.6 mmol) and benzyl bromide (9.7 g, 56.8 mmol) were added, and the mixture was stirred for 24 hours at ambient temperature. Diethyl ether (100 ml) was added and the mixture was washed with water (3×100 ml), dried with magnesium sulphate and 2-( 2-benzyloxyethyl)-1,3-dioxolane was distilled as a colourless oil. Yield 9.3 g (75%) b.p. 75°–78° C. (0.02 mm Hg). The structure was confirmed by $^1$H NMR and $^{13}$C NMR.

(c) 3-Benzyloxy-propanal

A mixture of 2-(2-benzyloxyethyl)-1,3-dioxalane (2.0 g, 9.6 mmol), 35% formaldehyde in water (100 ml), tetrahydrofuran (20 ml) and sulfuric acid (0.25 g) was stirred at 50° C. for 16 hours. The mixture was cooled to ambient temperature, diethyl ether (200 ml) was added and the organic phase was separated. The organic phase was washed with water (2×30 ml) and dried with magnesium sulphate and 3-benzyloxypropanal was distilled as a colourless oil. Yield 1.2 g (76%) . b.p. 150° C. (40 mm Hg) . The structure was confirmed by $^1$H NMR and $^{13}$C NMR.

1,13-Bisbenzyloxy-5,9-bisbenzyloxymethyl-4,7,10-triazatridecane 1,5-Diamino-1,5-dibenzyloxymethyl-3-azapentane (0.50 g, 1.5 mmol) was dissolved in methanol (20 ml). 3-Benzyloxypropanal (0.50 q, 3 mmol), sodium cyanoborohydride (0.11 g, 3 mmol) and 3 Å molecular sieve (10 g) were added and the mixture was stirred for 16 hours at ambient temperature. The reaction mixture was filtered, water (20 ml) was added and the mixture was acidified with hydrochloric acid to pH 3. The mixture was extracted with diethyl ether (2–25 ml), the ether solution was dried with magnesium sulphate, the solution was evaporated and the mixture was chromatographed on silica. 1,13-Bisbenzyloxy-5,9-bisbenzyloxymethyl- 4,7,10-triazatridecane was isolated as a white solid. Yield 0.40 g (42%), FAB MS: 640(M+1). The structure was confirmed by $^1$H NMR and $^{13}$C NMR.

(e) $N^4,N^7,N^{10}$-Triscarboxymethyl-1,13-bisbenzyloxy- 5,9-bisbenzyloxymethyl-4,7,10-triazatridecane 1,13-Bisbenzyloxy-5,9-bisbenzyloxymethyl-4,7,10-triazatridecane (0.37 g, 0.6 mmol) was dissolved in 2-propanol (5 ml). A solution of bromoacetic acid (0.33 g, 2.4 mmol), lithium hydroxide (0.10 g 2.4 mmol) in water (20 ml) was added. The temperature was gradually increased to reflux over five hours and kept at reflux for four hours. The reaction mixture was kept in the alkaline range during the alkylation. The solution was neutralised with concentrated hydrobromic acid and chromatographed on silica. $N^4,N^7,N^{10}$-Triscarboxymethyl-1,13-bisbenzyloxy- 5,9-bisbenzyloxymethyl-4,7,10-triazatridecane was isolated as a white solid. Yield 0.30 g (70%) m.p. 150° C. The structure was confirmed by $^1$H NMR and $^{13}$C NMR.

(f) $N^4, N^7, N^{10}$-Triscarboxymethyl-1,13-bishydroxyl- 5,9-bishydroxymethyl-4,7,10-triazatridecane $N^4,N^7,N^{10}$-Triscarboxymethyl-1,13-bisbenzyloxy- 5,9-bisbenzyloxymethyl-4,7,10-triazatridecane (0.30 g, 0.4 mmol) was dissolved in methanol (15 ml), 10% Palladium on carbon (0.3 g) and ammonium formate (0.1 g) were added and the mixture was kept at 50° C. for 16 hours. The catalyst was filtered off and washed with methanol (5 ml). The filtrate was evaporated and the title compound was isolated as a white powder. Yield 0.14 g (95%). M.p. 173°–177° C. The structure was confirmed by $^1$H NMR and $^{13}$CNMR.

EXAMPLE 8

$N^6$-Carboxymethyl-$N^3,N^9$-bis(methyl-carbamylmethyl)-4,8-bishydroxymethyl-3,6,9-triazaundecane diacid

(a) $N^6$-Carboxymethyl-$N^3,N^9$-bis(methyl-carbamylmethyl)-4,8-bisbenzyloxymethyl-3,6,9-triazaundecane diacid 3,6,9-Tris-carboxymethyl-4,8-bis-hydroxymethyl- 3,6,9-triazaundecanediacid (0.5 g, 0.79 mmol) (from Example 6) was dissolved in a mixture of pyridine (5 ml) and acetic anhydride (2 ml). The mixture was stirred at 65° C. under a nitrogen atmosphere for 16 hours. The solvent was evaporated and the residue was dissolved in a solution of dry methylamine in chloroform (1.5M, 50 ml). The mixture was stirred for 16 hours at ambient temperature. The solvent was evaporated and the product was purified on silica $N^6$-Carboxymethyl-$N^3,N^9$-bis(methyl carbamylmethyl)- 4,8-bis benzyloxymethyl-3,6,9-triazaundecane diacid was isolated as a colourless oil. Yield 0.30 g (57%). The structure was confirmed by $^1$H NMR and $^{13}$C NMR.

(b) $N^6$-Carboxymethyl-$N^3,N^9$-bis(methyl-carbamylmethyl)-4,8-bishydroxymethyl-3,6,9-triazaundecane diacid $N^6$-carboxymethyl-$N^3,N^9$-bis(methyl carbamylmethyl)-4,8-bis-benzyloxymethyl-3,6,9-triazaundecane diacid (0.30 g, 0.46 mmol) dissolved in methanol (15 ml) was added to ammonium formate (0.13 g) and 10% Palladium on carbon (0.20 g). The mixture was kept at 50° C. for 16 hours. The catalyst was filtered off and washed with methanol (5 ml). The filtrate was evaporated and the title compound was isolated as a white powder. Yield 209 mg, (95%). M.p. 130° C. The structure was confirmed by $^1$H NMR and $^{13}$C NMR.

EXAMPLE 9

3,6,9-Tris-carboxymethyl-4-(2-hydroxyethyl)-3,6,9-triazaundecane diacid

(a) 6-Amino-2-(2-hydroxyethyl)-3-oxo-1-(tris-triphenylmethyl)-1,4-diazahexane N-Triphenylmethyl-α-aminobutyrolactone (10 g, 29.1 mmol) (from Example 4) was dissolved in ethylenediamine (60 g, 1.0 mmol). The mixture was stirred at 50° C. for 16 hours. The excess of ethylenediamine was evaporated and the oily residue was dissolved in chloroform (100 ml) and washed with water (5×50 ml). The organic phase was dried with sodium sulfate and evaporated. The residue was dissolved in THF (100 ml) and left overnight at 4° C. The precipitate was washed with cold THF (10 ml) add dried. 6-Amino-2-(2-hydroxyethyl)-3-oxo-1-(tris-triphenyl-methyl)- 1,4-diazahexane was isolated as white crystals. Yield 8.8 g (75%) m.p. 160°–161° C. The structure was confirmed by 1HNMR and 13CNMR.

(b) 1,5-Diamino-2-(2-hydroxyethyl)-3-azaheptane trihydrochloride

6-Amino-2-(2-hydroxyethyl)-3-oxo-1-(tris-triphenylmethyl)- 1,4-diazahexane (8.8 g, 21.8 mmol) was dissolved in dry THF (distilled from lithium aluminium hydride) (10 ml). The solution was stirred under an inert atmosphere and cooled to 0° C. Lithium aluminium hydride (9.93 g, 261.9 mmol) was gradually added over 2 hours. The mixture was heated and was then refluxed for 24 hours. The reaction mixture was cooled to 0° C. and aqueous THF (10 ml water in 100 ml THF) was added dropwise. 2N Sodium hydroxide (10 ml) and water (10 ml) were added dropwise to the cooled mixture. After 2 hours the stirred suspension was filtered and the solid was washed thoroughly with THF (50 ml). The filtrate was evaporated to dryness, and the residue was eluted on silica with chloroform: methanol: ammonia in water to yield 4.5 g of a colourless oil.

The oil was dissolved in methanol (100 ml). Concentrated hydrochloric acid (10 ml) was added and the mixture was stirred at ambient temperature for 16 hours. The mixture was filtered and the filtrate was evaporated. The residue was extracted with a mixture of water (50 ml) and chloroform (50 ml). The aqueous phase was separated and evaporated. 1,5-Diamino-2-(2-hydroxyethyl)-3-azaheptane trihydrochloride was isolated as a white solid. Yield 2.8 g (50%).

FAB MS: 148(M+1). The structure was confirmed by 1HNMR and 13CNMR.

(c) 3,6,9-Tris-carboxymethyl-4-(2-hydroxyethyl)-3,6,9-triazaundecanediacid 1,5-Diamino-2-(2-hydroxyethyl)-3-azaheptane trihydrochloride (2,8 g, 11.0 mmol) was dissolved in water (10 ml). pH was adjusted to 10 with 4M lithium hydroxide, and a solution of bromoacetic acid (9.14 g, 66 mmol) and lithium hydroxide (2.8 g, 66 mmol) in water (20 ml) was gradually added to the stirred mixture at ambient temperature. The temperature was gradually increased to 85° C. during 4 hours while the pH was kept in the alkaline range (8 to 10) with aqueous lithium hydroxide. The solution was allowed to cool to ambient temperature, neutralised with concentrated hydrobromic acid, loaded on a strong cation exchanger (AG 5Wx4) and eluted with 6M aqueous ammonia with 25 mM ammonium formate. After evaporation the crude product was dissolved in water and lyophilised to yield 3.6 g (75%) of the title compound as a white solid. M.p. greater than 350° C., FAB MS: 440(M+1). The structure was confirmed by 1HNMR and 13CNMR.

EXAMPLE 10

3,9-Bis-(methylcarbamoylmethyl)-6-carboxymethyl-4-(2-hydroxy-ethyl)-3,6,9-triazaundecanediacid 3,6,9-Tris-carboxymethyl-4-(2-hydroxyethyl)-3,6,9-triazaundecanediacid (0.5 g, 1.13 mmol) was dissolved in a mixture of pyridine (5 ml) and acetic anhydride. The mixture was stirred under nitrogen for 16 hours at 65° C. The solvent was evaporated and the residue was dissolved in a solution of methylamine in chloroform (1.5M, 150 ml). The mixture was stirred in a pressure vial at 60° C. for 24 hours. The mixture was evaporated and the residue purified on a silica column. The title compound was isolated as a white powder. Yield 0.25 g (47%). FAB MS: 462(M+1). The structure was confirmed by $^1$HNMR and $^{13}$C NMR.

EXAMPLE 11

Gadolinium (III) Chelate of N-carboxymethyl-N,N-bis-((N'-carboxymethyl-N'-2,3-dihydroxypropyl)-2-aminoethyl)-amine To a solution of 42.5 g (0.1 mol) of N-carboxymethyl-N,N-bis-((N'-carboxymethyl-N'- 2,3-dihydroxypropyl)-2-aminoethyl)-amine (Example 1) in 300 ml water was added 18.1 g (0.05 mol) of gadolinium oxide Gd$_2$O$_3$ and the mixture was heated at 95° C. overnight. After filtration the solution was evaporated and dried in vacuo at 50 ° C.

Yield: 56.6 g (98%) (white powder) M.P. : greater than 350° C. Relaxivity: 5.0 mM$^{-1}$s$^{-1}$

EXAMPLE 12

Gadolinium (III) Chelate of N,N,N-tris-((N'-carboxymethylN'-2,3-dihydroxypropyl)-2-aminoethyl)-amine To a solution of 54.2 g (0.1 mol) of N,N,N-tris((N'-carboxymethyl-N'- 2,3-dihydroxypropyl)-2-aminoethyl)amine (Example 2) in 300 ml of water was added 18.1 g (0.05 mol) of gadolinium oxide Gd$_2$O$_3$ and the mixture was heated at 95° C. overnight. After filtration the solution was evaporated and dried in vacuo at 50° C.

Yield: 68.9 g (99%) (white powder) M.p. : greater than 350° C. Relaxivity: 5.2 mM$^{-1}$s$^{-1}$

EXAMPLE 13

Gadolinium (III) Chelate of 1-oxa-4,7,10-triazacyclododecane-N,N',N"-triacetic acid A solution of 1-oxa-4,7,10-triazacyclododecane-N,N',N"-triacetic acid (0.347 g (1 mmol)) (Example 3) in 10 ml water was heated to 80° C. An equimolar amount of gadolinium (III) chloride was added to the solution while the pH was continuously adjusted with 0.1N NaOH to be within the range 5.5–7. The temperature was maintained at 80° C. for two hours after the addition of the gadolinium chloride. The complex was isolated by evaporation to dryness.

Relaxivity: 4.6 mM$^{-1}$s$^{-1}$

EXAMPLE 14

Preparation of a solution containing gadolinium (III) chelate of N,N,N-tris((N'-carboxymethyl-N'-2,3-dihydroxypropyl)-2-aminoethyl)-amine 6.9 g of gadolinium (III) chelate of N,N,N-tris((N'-carboxymethyl-N'- 2,3-dihydroxypropyl)-2-aminoethyl)-amine (the product of Example 12) was dissolved in 20 ml of distilled water. The solution was filled in a 20 ml vial and autoclaved. The solution contained 0.5 mmol Gd/ml.

EXAMPLE 15

Preparation of a solution containing gadolinium (III) chelate of 1-oxa-4,7,10-triazacyclododecane-N,N',N"-triacetic acid 5.01 g of gadolinium (III) chelate of 1-oxa-4,7,10-triazacyclododecane-N,N',N"-triacetic acid (the product of Example 13) was dissolved in 20 ml of distilled water. The solution was filled in a 20 ml vial and autoclaved. The solution contained 0.5 mmol Gd/ml.

EXAMPLE 16

Preparation of a solution containing the disodium salt of the calcium chelate of 3,6-bis-(carboxymethyl)-4-hydroxyethyl-3,6-diazaoctanediacid 3,6-Bis(carboxymethyl)-4-hydroxyethyl-3,6-diazaoctanediacid (1.011 g, 3 mmol) (from Example 4) and calcium carbonate (300 mg, 3 mmol) were refluxed for 8 hours in water (15 ml). The mixture was cooled to ambient temperature, pH was adjusted to 7 by careful addition of 1N sodium hydroxide, water was added to 20 ml, the solution was filtered and filled into a 20 ml vial. The vial was autoclaved.

The solution contained 0.15 mmol calcium chelate of 3,6-bis-(carboxymethyl)-4-hydroxyethyl-3,6-diazaoctanediacid as disodium salt per ml.

The solution is for treatment of acute or chronic poisoning by heavy metals such as lead.

EXAMPLE 17

Vial containing
N³,N⁶,N⁹-tris-carboxymethyl-4,8-bis-hydroxymethyl-
3,6,9-triazaundecanediacid A vial is filled with N³,N⁶,N⁹-tris-carboxymethyl- 4,8-bishydroxymethyl-3,6-9-triazaundecanediacid (4 mg) (Example 6) and tin (II) chloride (0.22 mg) as dry powder.

A solution of $^{99m}$Tc as pertechnetate in 0.9% sterile sodium chloride should be added before use. The technetium chelate with N³,N⁶,N⁹-tris-carboxymethyl- 4,8-bis-hydroxymethyl-3,6,9-triazaundecanediacid is for intravenous administration and is a "contrast agent" for scintigraphic examination of organs like brain and kidneys. The chelate is also useful for study of kidney function.

EXAMPLE 18

Preparation of a solution of containing the
disodium salt of the zinc chelate of
3,6,9-tris-carboxymethyl-
4-(2-hydroxyethyl)-3,6,9-triazaundecanediacid 3,6,9-Tris-carboxymethyl-4-(2-hydroxyethyl)-3,6,9-triazaundecanediacid (878 mg, 2 mmol) (Example 9) and zinc (II) carbonate (251 mg, 2 mmol) were refluxed for 12 hours in water (15 ml). The mixture was cooled to ambient temperature, the pH was adjusted to 6 by careful addition of 1N sodium hydroxide, water was added to 20 ml, the solution was filtered and filled into a 20 ml vial. The vial was autoclaved. The solution contained 0.1 mmol of the zinc chelate as disodium salt per ml.

The solution is for treatment of acute or chronic poisoning by heavy metals such as lead and radioactive metals such as plutonium.

EXAMPLE 19

Preparation of a solution containing chromium (III)
chelate of 3,6-bis-(carboxymethyl)-4-hydroxyethyl-
3,6-diazaoctane-diacid 3,6-Bis-(carboxymethyl)-4-hydroxyethyl-3,6-diazaoctanediacid (97 mg, 0.3 mmol) (Example 4) was dissolved in water (10 ml). Chromium (III) chloride hexahydrate (80 mg, 0.3 mmol) in water (2 ml) was added, and the mixture was stirred at 65° C. for 1 hour. During the first 30 minutes N-methyl glucamine (234 mg, 1.2 mmol) was gradually added to keep pH at approximately 6. The mixture was cooled to ambient temperature and water was added to a total volume of 20 ml. The solution was filtered, filled into a 20 ml vial and autoclaved.

The concentration of chromium (III) chelate of 3,6-bis-(carboxymethyl)-4-hydroxyethyl-3,6-diazaoctanediacid was 15 mmolar.

EXAMPLE 20

Bismuth (III) chelate of
1-thia-4,7,10-triazacyclododecane triacetic acid

A neutral suspension of bismuth hydroxide was prepared by neutralisation of an acidic solution of bismuth chloride (52.03 mg, 0.165 mmol) with sodium hydroxide followed by centrifugation of the precipitate and resuspension of the precipitate in water (2 ml). This suspension was added to a solution of 1-thia-4,7,10-triazacyclododecane triacetic acid (60 mg, 0.165 mmol) (Example 5) in water (2 ml) and the mixture was stirred at 80° C. until complete dissolution (approximately 48 hours). The water was evaporated and the title compound isolated as a white solid. Yield 94 mg (99%) m.p. 190°–220° C., lambda max.=304 nm.

EXAMPLE 21

3,6-Bis-(carboxymethyl)-4-hydroxymethyl-3,6-
diazaoctanediacid (a) 2-Benzyloxymethyl-2-hydroxy-1-
phthalimido-ethane Freshly distilled benzyl-glycidylether (60 g, 0.365 mmol), phthalimide (49.2 g, 0.304 mmol) and potassium carbonate (3.34 g, 24 mmol) were refluxed with stirring in ethanol (500 ml) for 27 hours. TLC indicated full conversion of the starting material. Ethanol was removed in vacuo. The residual oily material was transferred to a 2 l separation funnel and distributed between ethyl acetate (800 ml) and water (500 ml). The aqueous phase was extracted with ethyl acetate (200 ml), and the combined organic phases were washed with water (300 ml), dried over magnesium sulphate, filtered and concentrated in vacuo. The residual oily material (115 g) was diluted with an equal amount (w/v) of ether (115 ml) and allowed to stand for several days. Crystals were collected on a glass sinter and air dried with suction for 1 hour; then dried under vacuum to constant weight. Yield: 81.5 g (72%). The mother liquor was diluted with ether and seeded with crystals from the first crop. Total yield: 80%. TLC indicated one spot. Structure was confirmed by NMR and IR.

(b) 2-Benzylmethyl-2-(trifluoromethylsulfonyloxy)-
1-phthalimido-ethane

2-Benzyloxymethyl-2-hydroxy-1-phthalimido-ethane (20 g, 64 mmol) was dissolved in dichloromethane (180 ml), and pyridine (12.2 g, 154 mmol) was added. The mixture was cooled to −13°/−15° C. for 15 minutes—then trifluoromethylsulphonyloxy anhydride (triflic anhydride) (22 g, 76 mmol) was added. Without further cooling, the reaction proceeded for 3 hours. TLC indicated full conversion of starting material.

The reaction mixture was transferred to a 1 l separation funnel containing dichloromethane (60 ml) and 2M HCl (100 ml), and shaken. The aqueous phase was extracted with dichloromethane (45 ml); the combined organic phases were washed with 2M hydrochloric acid (100 ml), saturated aqueous sodium hydrogen carbonate (100 ml) and water (100 ml), dried over magnesium sulphate, filtered and concentrated in vacuo to a pale orange solid. Yield: 28.1 g (99%). TLC indicated one spot, and the structure was confirmed by NMR and IR.

(c) 2-Benzyloxymethyl-2-azido-
1-phthalimido-ethane

2-Benzyloxymethyl-2-(trifluoromethylsulfonyloxy)-1-phthalimido-ethane (8.5 g, 19.1 mmol) and sodium azide (2.5 g, 38.2 mmol) were stirred in dimethylformamide (80 ml) at 60° C. for 6 hours Under nitrogen. TLC in several systems was inconclusive because the Rf of the product was identical to the Rf of the starting material. A small sample was worked up and IR indicated full conversion to the azide. The reaction mixture was transferred to a 1 l extraction funnel and distributed between ethyl acetate (350 ml) and water (130 ml). The aqueous phase was extracted with ethyl acetate (80 ml); the combined organic phases were washed with water (2×120 ml), dried over magnesium sulphate, filtered and concentrated in vacuo to a pale brown oil. Crystallisation was initiated by adding ether (7 ml). Crystals were collected on a glass sinter, washed with cold ether and dried under vacuum for 28 hours. Yield: 4.5 g (70%). The mother liquors were concentrated, diluted with ether and seeded with crystals from the first crop—yielding another 1 g. Total yield: 5.5 g (85%). The structure was confirmed by NMR and IR.

(d) 2-Amino-2-benzyloxymethyl-1-phthalimido-ethane

Into a stirred solution of 2-benzyloxymethyl-2-azido-1-phthalimido-ethane (500 mg, 1.5 mmol) in 4:1 pyridine/water (25 ml) was bubbled hydrogen sulphide, and the reaction was monitored by TLC. After 4 hours, the gas flow was stopped, and the reaction flask sealed. The intense green reaction mixture was stirred for another 17 hours. TLC indicated full conversion of the starting material. Glacial acetic acid was added to pH 7, and the reaction mixture was evaporated to dryness in vacuo. After evaporation from ethanol (3×25 ml), the resulting brown solid was purified by chromatography. Yield=20%. The structure was confirmed by NMR and IR.

(e) 1,2-Diamino-1-benzyloxymethyl-ethane-dihydrochloride

1-Amino-2-benzyloxymethyl-1-phthalimido-ethane (3.0 g, 9.7 mmol) is dissolved in 50 ml dry methanol and hydrazine hydrate (968 mg, 19.3 mmol) is added. After being refluxed for 4 hours, the reaction mixture is stirred for 24 hours at ambient temperature and 50 ml 2N hydrochloric acid was added. The phthalhydrazide is removed by filtration and the 1,2-diamino- 1-benzyloxymethyl-ethane-dihydrochloride is purified by recrystallisation from dry ethanol.

(f) 4-Benzyloxymethyl-3,6-bis-carboxymethyl-diazaoctanediacid 1,2-Diamino-2-benzyloxymethyl-ethane-dihydrochloride (1.2 g, 4.74 mmol) is dissolved in water (10 ml), and the pH is adjusted to 9.5 with lithium hydroxide. Bromoacetic acid lithium salt (3.49 g, 23.7 mmol) is added and the mixture is heated to 50° C. and stirred at this temperature for 24 hours. During this period the pH is kept constant (9–10) by adding a solution of lithium hydroxide (1M). The mixture is cooled to ambient temperature and applied to a Biorad AG 50W-X4 column (80 ml) and eluted with water and aqueous saturated ammonia. 4-Benzyloxy-methyl- 3,6-bis-carboxymethyl-diazaoctane-diacid is isolated as a yellow solid.

(g) 3,6-Bis-(carboxymethyl)-4-hydroxymethyl-3,6-diazaoctanediacid

4-Benzyloxymethyl-3,6-bis-carboxymethyl-diazaoctanediacid (1.0 g, 2.4 mmol) is dissolved in methanol (20 ml) and 10% Palladium on carbon (5 g) is added. The mixture is kept at 50° C. overnight, filtered and evaporated. The crude product is applied to a AG 50W-X4 column, washed with methanol:water (1:1) and eluted with 6M aqueous ammonia. The title compound is isolated as a white powder.

EXAMPLE 22

1-(5-Hydroxy-3-oxapentyl)-1,4,7,10-tetraazacyclododecane-4,7,10-triacetic acid

(a) 1,4,7,10-Tetraazacyclododecane-4,7,10-triacetic acid tri-t-butyl ester

Sodium acetate (1.23 g, 15 mmol) was added to a stirred suspension of 1,4,7,10 tetraazacyclododecane (0.864 g, 5 mmol) (prepared in accordance with J. Am. Chem. Soc. 96 2268 (1974) and Liebigs Ann. Chem. 1340 (1977)) in N, N-dimethylacetamide (DMA) (15 ml) at ambient temperature. A solution of bromoacetic acid t-butyl ester (2.93 g, 15 mmol) in DMA (8 ml) was added dropwise to the stirred mixture, and the mixture was stirred at ambient temperature for 6 days. The solvent was evaporated and 1,4,7,10-tetraazacyclododecane- 4,7,10-triacetic acid tri-t-butyl ester was purified by flash chromotography on a silica column with chloroform:methanol 8:2 as eluent. Yield 1.8 g (70%). White solid, m.p. 165°–175° C.

(b) 1-(5-Hydroxy-3-oxapentyl)-1,4,7,10-tetraazacyclododecane-4,7,10-triacetic acid 1,4,7,10-Tetraazacyclododecane-4,7,10-triacetic acid tri-t-butyl-ester (515 mg, 1 mmol) was dissolved in dimethylformamide (3 ml). Sodium iodide (15 mg, 0.1 mmol), triethylamine (233 mg, 2.5 mmol) and 2(2-chloroethoxy-)ethanol (313 mg, 3.5 mmol) were added to the stirred mixture at ambient temperature. The mixture was stirred for 18 hours at ambient temperature. The temperature was then raised to 100° C. and kept there for 1 hour. The solvent was then evaporated and the residue dissolved in a mixture of dichloromethane (4.5 ml) and trifluoroacetic acid (4.5 ml). The mixture was stirred for 2 hours at ambient temperature and the solvent was then evaporated. The residue was dissolved in water (8 ml), and this aqueous solution was washed with ether (6–4 ml). The aqueous solution was acidified and the title compound was isolated as a hygroscopic white powder after evaporation of the water. Yield 325 mg (75%), FAB MS: 435(M+1). The structure was confirmed by $^1$HNMR and $^{13}$C NMR.

EXAMPLE 23

1-(8-Hydroxy-3,6-dioxaoctyl)-1,4,7,10-tetraazacyclododecane-4,7,10-triacetic acid 1,4,7,10-Tetraazacyclododecane-4,7,10-triacetic acid tri-t-butyl ester (129 mg, 0.25 mmol) (Example 22(a)) was dissolved in dimethylformamide (1 ml). Sodium iodide (7.5 mg, 0.5 mmol) , triethylamine (76 mg, 0.75 mmol) and 2-[2-(2-chloroethoxy)-ethoxy]ethanol (85 mg, 0.5 mmol) were added to the stirred mixture at ambient temperature. The mixture was stirred at ambient temperature for 90 minutes, the temperature was then raised to 100° C. and kept there for 1 hour. The solvent was evaporated, and the residue was dissolved in dichloromethane (2 ml) and washed with water (1 ml). Trifluoroacetic acid (2 ml) was added to the organic phase and the mixture was stirred at ambient temperature for 1 hour. The solvents were evaporated and the residue dissolved in water (4 ml). The aqueous solution was acidified, the water was evaporated and the title compound was isolated as a hygroscopic white powder. Yield 77 mg (64%). The structure was confirmed by $^1$HNMR and $^{13}$CNMR.

EXAMPLE 24

1-(2-Hydroxy-propyl)-1,4,7,10-tetraazacyclododecane-4,7,10-triacetic acid 1,4,7,10-Tetraazacyclododecane-4,7,10-triacetic acid tri-t-butyl ester (129 mg, 0.25 mmol) (Example 22(a)) was dissolved in dimethylformamide. Sodium iodide (7.5 mg, 0.5 mmol), triethylamine (76 mg, 0.75 mmol) and 3-chloro-2-propanol (48 mg, 0.5 mmol) were added to the stirred mixture at ambient temperature. The mixture was stirred for 4 hours at ambient temperature, the temperature was then raised to 100° C. and kept there for 2 hours. The solvent was evaporated, and the residue was dissolved in dichloromethane (2 ml) and washed with water (1 ml). Trifluoroacetic acid (2 ml) was added to the organic phase and the mixture was stirred at ambient temperature for 1 hour. The solvents were evaporated and the residue dissolved in water (4 ml). The aqueous solution was washed with ether (5×2 ml). The aqueous solution was acidified, the water was evaporated, and the title compound was isolated as a hygroscopic white powder. Yield 75 mg (74%) The structure was confirmed by $^1$HNMR and $^{13}$CNMR.

EXAMPLE 25

1-(3-Hydroxy-propyl)-1,4,7,10-tetraazacyclododecane-4,7,10-triacetic acid 1,4,7,10-Tetraazacyclododecane-4,7,10-triacetic acid tri-t-butyl ester (360 mg, 0.70 mmol) (Example 22(a)) was dissolved in dimethylformamide (2.1 ml). Sodium iodide (15 mg, 1 mmol), triethylamine (142 mg, 1.4 mmol) and 3-chloro-1-propanol (132 mg, 1.4 mmol) were added to the stirred mixture at ambient temperature. The mixture was stirred for 3 hours at ambient temperature, the temperature was then raised to 100° C. and kept there for 2 hours. The solvent was evaporated and the residue was dissolved in dichloromethane (3 ml) and washed with water (1 ml). Trifluoroacetic acid (2 ml) was added to the dichloromethane solution and the mixture was stirred at ambient temperature for 1 hour. The solvents were evaporated and the residue dissolved in water (6 ml). The aqueous solution was washed with ether (6×3 ml). The aqueous solution was acidified, the water was evaporated, and the title compound was isolated as a hygroscopic white powder. Yield 192 mg (68%), FAB MS: 405(M+1). The structure was confirmed by $^1$HNMR and $^{13}$CNMR.

EXAMPLE 26

Gd (III) chelate of 1-(5-hydroxy-3-oxa-pentyl)-1,4,7,10-tetraazacyclododecane-4,7,10-triacetic acid 1-(5-Hydroxy-3-oxapentyl)-1,4,7,10-tetraazacyclododecane-4,7,10-triacetic acid (400 mg) (Example 22) was dissolved in water (15 ml) and the pH was adjusted to 5.9. Gadolinium acetate tetrahydrate (203 mg, 0.5 mmol) was added and the mixture was stirred at 60° C. for 12 hours. The cooled aqueous solution was eluted through a mixed ion exchanger, the water was evaporated and the title compound was isolated as a white powder. Yield 212 mg (72%).

EXAMPLE 27

Bismuth (III) chelate of $N^3,N^6,N^9$-tris-carboxymethyl-4,8-bis-hydroxymethyl-3,6,9-triazaundecanediacid A neutral suspension of bismuth hydroxide was prepared by neutralisation of an acidic solution of bismuth chloride (69.4 mg, 0.22 mmol) in water (3 ml) with sodium hydroxide solution followed by centrifugation of the precipitate and resuspension of the precipitate in water (2 ml). This suspension was added to a solution of $N^3,N^6,N^9$-tris-carboxymethyl-4,8-bis-hydroxymethyl- 3,6,9-triazaundecanediacid (100 mg, 0.22 mmol) (Example 6) in water (20 ml). The pH was adjusted to 5.0 with sodium hydroxide solution, and the mixture was stirred at 95° C. for 12 hours and refluxed for 7 hours. The water was evaporated and the title compound was isolated as a white-solid. Yield 139 mg (95%).

EXAMPLE 28

Gadolinium (III) chelate of $N^3,N^6,N^9$-tris-carboxymethyl-4,8-bis-hydroxymethyl-3,6,9-triazaundecanediacid A solution of gadolinium acetate tetrahydrate (89 mg, 0.22 mmol) in water (4 ml) was added to a stirred solution of $N^3,N^6,N^9$-tris-carboxymethyl-4,8-bis-hydroxymethyl-3,6,9-triazaundecanediacid (100 mg, 0.22 mmol) (Example 6) in water (20 ml) at ambient temperature (pH 5.7). The mixture was stirred for 90 minutes at 95° C., the solvent was evaporated and the title compound was isolated as a white powder. Yield 128 mg (98%), FAB MS: 608(M+1).

EXAMPLE 29

Gadolinium (III) chelate of 1-thia-4,7,10-triazacyclo-dodecane triacetic acid A solution of gadolinium acetate tetrahydrate (0.13 g, 0.33 mmol) in water (3 ml) was added to a stirred solution of 1-thia-4,7,10-triazacyclododecane triacetic acid (0.12 g, 0.33 mmol) (Example 5) in water (2 ml) at ambient temperature. The pH was adjusted to 5.5 by addition of 0.1N ammonia solution and the mixture was stirred at 70° C. for 22 hours (with repeated adjustment of pH). The solvent was evaporated and the title compound was isolated as a white powder. Yield 0.168 g (98%) m.p. greater than 350° C.

EXAMPLE 30

Manganese (II) chelate of 1-thia-4,7,10-triazacyclododecane triacetic acid

1-Thia-4,7,10-triazacyclododecane triacetic acid (0.727 g, 2 mmol) (Example 5) was dissolved in water (20 ml), and the pH was adjusted to 5.8 with 1N hydrochloric acid. Manganese carbonate (0.230 g, 2 mmol) was added and the suspension was stirred at 100° C. until complete dissolution. The water was evaporated and the title compound isolated as a white hygroscopic powder. Yield 0.81 g (98%).

EXAMPLE 31

Fe(III) chelate of 1-(8-hydroxy-3,6-dioxaoctyl)-1,4,7,10-tetraazacyclododecane-4,7,10-triacetic acid 1-(8-Hydroxy-3,6-dioxaoctyl)-1,4,7,10-tetraazacyclododecane- 4,7,10-triacetic acid (72 mg, 0.15 mmol) (Example 23) was dissolved in water (5 ml). Iron (III) chloride (24.3 mg, 0.15 mmol) was dissolved in water (5 ml), and added to the above solution. The pH was adjusted to 4 and the mixture was stirred at 100° C. for 30 minutes. The water was evaporated and the title compound isolated as a brown hygroscopic powder. Yield 77 mg (97%).

EXAMPLE 32

5,9-Bis(hydroxymethyl)-1-oxa-4,7,10-triazacyclododecane-4,7,10-triacetic acid

(a) Diglycolic acid dimethyl ester

Diglycolic acid (67.05 g, 0.5 mol) was dissolved in a mixture of methanol (122 ml, 30 mol) and 1,2-dichloroethane (150 ml). KSF-catalyst (Aldrich) (2.5 g) was added and the mixture was refluxed for 15 hours. The mixture was cooled to ambient temperature, filtered through alumina, washed with aqueous saturated sodium hydrogen carbonate (100 ml) and dried over magnesium sulphate. The solvent was evaporated and diglycolic acid dimethyl ester was isolated after distillation as a colourless oil. Yield 39.5 g (49%) b.p. 65°–66° C. (0.055 mmHg).

(b) Diglycolic acid dichloride

Dimethylformamide (10 drops) was added to a stirred solution of diglycolic acid (13.4 g, 0.1 mmol) in thionyl chloride (50 ml) at ambient temperature. The mixture was stirred for 2 hours at 50° C. and excess thionyl chloride was evaporated and the last trace of thionyl chloride was removed azeotropically with benzene. Diglycolic acid dichloride was isolated as a colourless oil. Yield 13.7 g (80%), b.p. 116° C. (15 mm Hg).

(c) 5,9-Bis(benzyloxymethyl)-1-oxa-4,7,10-triazacyclododecane-3,11-dione (Alternative 1)

1,5-Diamino-1,5-dibenzyloxymethyl-3-aza-pentane (0.250 g, 0.73 mmol) (Example 6 (d)) and diglycolic acid dimethyl ester (0.118 g, 0.73 mmol) were dissolved in methanol (20 ml). The mixture was refluxed for 6 days. The solvent was evaporated and the mixture chromatographed on a silica column. 5,9-Bis(benzyloxymethyl)- 1-oxa-4,7,10-triazacyclododecane- 3,11-dione was isolated as a yellow oil. Yield 0.273 g (85%). FAB MS: 442(M+1).

(d) 5,9-Bis(benzyloxymethyl)-1-oxa-4,7,10-triazacyclododecane-3,11-dione (Alternative 2)

A solution of 1,5-diamino-1,5-dibenzyloxymethyl-3-azapentane (0.57 g, 1.7 mmol) (Example 6(d)) and triethylamine (0.34 g, 3.4 mmol) in dichloromethane (10 ml) and a solution of diglycolic acid dichloride (0.29 g, 1.7 mmol) in dichloromethane (10 ml) were added simultaneously over 2.5 hours to vigorously stirred dichloromethane (10 ml) at 0° C. The solution was stirred at ambient temperature overnight, washed with water (2×30 ml), dried with sodium sulphate and evaporated. Yield 0.59 g (78%).

(e) 5,9-Bis-(benzyloxymethyl)-1-oxa-4,7,10-triazacyclododecane 5,9-Bis-(benzyloxymethyl)-1-oxa-4,7,10-triazacyclododecane- 3,11-dione (0.250 g, 0.566 mmol) was dissolved in dry tetrahydrofuran (10 ml) cooled to 0° C. A 1M solution of borohydride-THF complex in tetrahydrofuran (5 ml) was added under nitrogen and the mixture was stirred at ambient temperature for 14 hours. 2M Hydrochloric acid (3 ml) was added and the mixture was concentrated in vacuo to approximately 1 ml volume. 25% Ammonia solution (2 ml) was added and the mixture was extracted four times with 4 ml of chloroform. The extracts were concentrated in vacuo and gave a yellow oil which showed an absence of carbonyl bands in IR. Yield 0.227 g (97%), FAB MS: 414 (M+1).

(f) 5,9-Bis-(hydroxymethyl)-1-oxa-4,7,10-triazacyclododecane 5,9-Bis(benzyloxymethyl)-1-oxa-4,7,10-triazacyclododecane (0.24 g, 0.6 mmol) was dissolved in methanol (10 ml). Ammonium formate (0.20 g, 3 mmol) and 10% Palladium on carbon (0.40 g) were added and the mixture was stirred under a nitrogen atmosphere at 50° C. for 16 hours. The catalyst was filtered off and washed with methanol (5 ml). The filtrate was evaporated and the 5,9-Bis-(hydroxymethyl)- 1-oxa-4,7,10-triazacyclododecane was isolated as a colourless oil. Yield 0.12 g (86%).

(g) 5,9-Bis(hydroxymethyl)-1-oxa-4,7,10-triazacyclododecane-4,7,10-triacetic acid 5,9-Bis-(hydroxymethyl)-1-oxa-4,7,10-triazacyclododecane (0.12 g, 0.5 mmol) was dissolved in water (2 ml). The pH was adjusted to 10 with 4M lithium hydroxide, and a solution of bromoacetic acid (0.21 g, 1.5 mmol) and lithium hydroxide (0.06 g, 1.5 mmol) in water (2 ml) was gradually added.

The temperature was gradually increased to 85° C. during 6 hours while the pH was kept in the alkaline range with aqueous lithium hydroxide. The solution was allowed to cool to ambient temperature, neutralised with concentrated hydrobromic acid, loaded on a strong cation exchanger (AG50Wx4) and eluted with 6M aqueous ammonia with 50 mM ammonium formate. The solution is concentrated by lyophilization and the title compound isolated. Yield: 0.09 g, (42%).

EXAMPLE 33

5,9-Bis(hydroxymethyl)-1-thia-4,7,10-triazacyclododecane triacetic acid

(a) 5,9-Bis(benzyloxymethyl)-1-thia-4,7,10-triazacyclododecane-3,11-dione 1,5-Diamino-1,5-dibenzyloxymethyl-3-azapentane (0.282 g, 0.82 mmol) (Example 6(d)) and thiodiglycolic acid dimethyl ester (0.146 g, 0.82 mmol) (Example 5(a)) were dissolved in methanol (20 ml). The mixture was refluxed for 6 days. The solvent was evaporated and 5,9-bis(benzyloxymethyl)-1-thia-4,7,10-triazacyclododecane- 3,11-dione was isolated as a yellow oil after chromatography on a silica column. Yield 0.352 g (94%) FAB MS: 458(M+1).

(b) 5,9-Bis(benzyloxymethyl)-1-thia-4,7,10-triazacyclododecane 5,9-Bis(benzyloxymethyl)-1-thia-4,7,10-triazacyclododecane- 3,11-dione (0.352 g, 0.769 mmol) was dissolved in dry THF (10 ml) and cooled to 0° C. A 1M solution of borohydride –THF complex in THF (5 ml) was added under nitrogen and the mixture was stirred for 1 hour at ambient temperature and refluxed for 0.5 hours. To the cooled solution was added 2M hydrochloric acid (3 ml) and the resulting mixture was evaporated to dryness. Water (1 ml) and 25% ammonia solution (1 ml) was added and the mixture was extracted 3 times with 4 ml chloroform. The combined extracts were concentrated in vacuo and gave a yellow oil which showed absence of carbonyl bands in IR. Yield: 0.29 g (88%), FAB MS: 430(M+1).

(c) 5,9-Bis(hydroxymethyl)-1-thia-4,7,10-triazacyclododecane 5,9-Bis(benzyloxymethyl)-1-thia-4,7,10-triazacyclododecane (0.28 g, 0.65 mmol) was dissolved in methanol (10 ml). Ammonium formate (0.39 g) and 10% Palladium on carbon (1.3 g) were added under nitrogen and the mixture was stirred at 50° C. for 16 hours. The catalyst was filtered off and washed with methanol (5 ml). The filtrate was evaporated and 5,9-bis(hydroxymethyl)- 1-thia-4,7,10-triazacyclododecane was isolated as a white solid. Mp. 210°–220° C. (subl.). Yield: 0.099 g (61%).

(d) 5,9-Bis(hydroxymethyl)-1-thia-4,7,10-triazacyclododecane triacetic acid 5,9-Bis(hydroxymethyl)-1-thia-4,7,10-triazacyclododecane (0.090 g, 0.361 mmol) is dissolved in water (2 ml). The pH is adjusted to 10 with 4M lithium hydroxide, and a solution of bromoacetic acid (0.170 g, 1,226 mmol) in water (2 ml) is gradually added. The temperature is gradually increased to 85° C. during 4 hours while the pH is kept in the alkaline range (8 to 10) with aqueous lithium hydroxide. The solution is allowed to cool to ambient temperature, neutralised with concentrated hydrobromic acid, loaded on a strong cation exchanger (AG 50Wx4) and eluted with 6M aqueous ammonia with 25 mM ammonium formate. The solution is evaporated and the title compound is isolated.

EXAMPLE 34

Preparation of a solution containing the calcium salt of the gadolinium (III) chelate of $N^3,N^6,N^9$-triscarboxymethyl-4,8,bishydroxymethyl-3,6,9-triazaundecanediacid Gadolinium (III) chelate of $N^3,N^6,N^9$-triscarboxymethyl-4,8-bis-hydroxymethyl-3,6,9-triazaundecanediacid (607 mg, 1 mmol) (Example 28) and calcium hydroxide (74 mg, 1 mmol) were suspended in water (8 ml). The mixture was refluxed for 5 hours, the pH was adjusted to 7.0 and water (to 10 ml) was added. The solution was filtered and filled into a 10 ml vial. The vial was autoclaved. The solution contained 0.1 mmol Gd per ml.

EXAMPLE 35

Preparation of a solution containing the di-lysine salt of the gadolinium (III) chelate of $N^3,N^6,N^9$-triscarboxymethyl-4,8-bishydroxymethyl-3,6,9-triazaundecanediacid Gadolinium (III) chelate of $N^3,N^6,N^9$-triscarboxymethyl-4,8-bis-hydroxymethyl-3,6,9-triazaundecanediacid (3.04 g, 5 mmol) (Example 28) and lysine (2.92 g, 10 mmol) were suspended in water (8 ml). The mixture was refluxed for 4 hours, the pH was adjusted to 7.0 and water (to 10 ml) was added. The solution was filtered and filled into a 10 ml vial. The vial was autoclaved. The solution contained 0.5 mmol Gd per ml.

EXAMPLE 36

$N^6$-Carboxymethyl-$N^3$,$N^9$-bis(2,3-dihydroxypropyl-carbamyl-methyl)-4,8-bis(hydroxymethyl)-3,6,9-triazaundecane diacid

(a) $N^6$-Carboxymethyl-$N^3$,$N^9$-bis(2,3-dihydroxypropyl-carbamylmethyl)-4,8-bis(benzyloxymethyl)-3,6,9-triazaundecane diacid 3,6,9-Tris-carboxymethyl-4,8-bis(benzyloxymethyl)- 3,6,9-triazaundecanediacid (0.5 g, 0.79 mmol) (Example 6) was dissolved in a mixture of pyridine (5 ml) and acetic anhydride (2 ml). The mixture was stirred at 65° C. under a nitrogen atmosphere for 16 hours. The solvent was evaporated and the residue was dissolved in dimethylformamide (5 ml). A solution of 1-amino- 2,3-propanediol (0.7 g, 7.8 mmol) in dimethylformamide (2 ml) was added. The solution was stirred for 16 hours and the solvent and excess reagent were evaporated. $N^6$-Carboxymethyl-$N^3$,$N^9$-bis(2,3-dihydroxypropylcarbamylmethyl)- 4,8-bis(benzyloxymethyl)-3,6,9-triazaundecane diacid was isolated as a colourless oil. Yield 0.32 g (52%). The structure was confirmed by $^1$H NMR and $^{13}$C NMR.

(b) $N^6$-Carboxymethyl-$N^3$,$N^9$-bis(2,3-dihydroxypropylcarbamylmethyl)-4,8-bis(hydroxymethyl)-3,6,9-triazaundecane diacid $N^6$-Carboxymethyl-$N^3$,$N^9$-bis(2,3-dihydroxypropyl-carbamylmethyl)- 4,8-bis(benzyloxymethyl)-3,6,9-triazaundecane diacid (0.32 g, 0.41 mmol) was dissolved in methanol (15 ml). Ammonium formate (0.13 g) and 10% Palladium on carbon (0.20 g) were added and the mixture was stirred at 50° C. for 16 hours. The catalyst was filtered off and washed with methanol (5 ml). The filtrate was evaporated and the title compound was isolated as a colourless oil. Yield 0.23 g (95%). The structure was confirmed by $^1$H NMR and $^{13}$C NMR.

EXAMPLE 37

Solution containing gadolinium (III) chelate of 1-oxa-4,7,10-triazacyclododecane-N,N',N"-triacetic acid for parenteral administration

| | |
|---|---|
| Gadolinium (III) chelate of 1-oxa-4,7,10-triazacyclododecane-N,N',N"-triacetic acid (Example 13) | 0.50 g |
| Saccharin sodium | 1.0 g |
| Ethanol | 10.0 g |
| Orange essence | 0.3 g |
| Apricot essence | 0.7 g |
| Water | ad 1000 ml |

Gadolinium (III) chelate of 1-oxa-4,7,10-triazacyclododecane-N,N',N"-triacetic acid was dissolved in water (500 ml). The essences were dissolved in ethanol and slowly added to the aqueous solution. Water was added to bring the volume to 1000 ml and the solution was filled into a 1000 ml vial. The solution contained 1 mmol gadolinium per liter.

EXAMPLE 38

2-(2-Hydroxyethyl)-1,4,7,11-tetrakis-carboxymethyl-1,4,7,11-tetraazacyclododecane (a) 2-(2-Hydroxyethyl)-3-oxo-1,7-bis(triphenylmethyl)-1,4,7-triazaheptane 6-Amino-2-(2-hydroxyethyl)-3-oxo-1-(triphenylmethyl)-1,4-diazahexane (15.0 g, 37.2 mmol) (Example 9(a)) was dissolved in 150 ml DMF and triphenylmethyl chloride (10.35 g, 37.2 mmol) and methylmorpholine (3.75 g, 37.2 mmol) was added. After being stirred for 24 hours at ambient temperature, the reaction mixture was filtered and poured into 200 ml of ice water. After 1 hour stirring, filtration and thoroughly washing the precipitate with water, the solid was dried in vacuo at 50° C. to yield 22 g of crude product. The product was dissolved in chloroform/toluene/methanol (80/16/14) and purified on silica to yield 6.6 g (27%) of 2-(2-hydroxyethyl)- 3-oxo-1,7-bis(triphenylmethyl)-1,4,7-triazaheptane as white crystals, m.p. 71°–72° C., FAB MS: 646(M+1). The structure was confirmed by $^{13}$C NMR.

(b) 2-(2-Benzyloxyethyl)-3-oxo-1,7-bis(triphenylmethyl)-1,4,7-triazaheptane 2-(2-Hydroxyethyl)-3-oxo-1,7-bis(triphenylmethyl)- 1,4,7-triazaheptane (10 mmol) is reacted as described by S. Czernecki et al. Tetr. Lett. (1976) 3535 with 80% sodium hydride (11 mmol) and benzylbromide (10 mmol) catalysed by tetrabutyl ammonium iodide (1 mmol) for 24 hours at ambient temperature (in 100 ml dry THF). 2-(2-Benzyloxyethyl)-3-oxo-1,7-bis(triphenylmethyl)- 1,4,7-triazaheptane is purified by chromatography on silica.

(c) 1,5-Diamino-1-(2-benzyloxyethyl)-3-aza-pentane hydrochloride 2-(2-Benzyloxyethyl)-3-oxo-1,7-bis(triphenylmethyl)-1,4,7-triazaheptane is reacted in a manner analogous to the reaction of step (c) of Example 9 up to the point where the purified product is taken up in methanol and conc. hydrochloric acid is added. From this point the method described by M. Bessodes et al., Tetr. Lett., (1986) 579 to remove the triphenylmethyl protecting groups is employed: the product is taken up in a mixture of formic acid and diethylether and refluxed for several hours. After evaporation to dryness the product is dissolved in water, the pH is adjusted to 10 and the product is extracted with chloroform. The organic phase is evaporated and the product is taken up in dry ethanol. Dry hydrogen chloride gas is bubbled through the stirred solution cooled with an ice/water bath, and 1,5-diamino-1-(2-benzyloxy-ethyl)- 3-azapentane hydrochloride is collected by filtration.

(d) 2-(2-Benzyloxyethyl)-tris-1,4,7-(4-methylbenzenesulphonyl)-1,4,7-triazaheptane 1,5-Diamino-1-(2-benzyloxy-ethyl)-3-aza-pentane hydrochloride (10 mmol) is dissolved in 20 ml of water and the pH is adjusted to 10.5. Tosyl chloride (30 mmol) dissolved in ether 415 ml) is added dropwise while the reaction mixture is vigorously stirred at ambient temperature for 24 hours. The ether phase is gradually evaporated to a minimum and the white solid is collected and purified on silica to yield 2-(2-benzyloxyethyl)-tris-1,4,7-(4-methylbenzenesulphonyl)- 1,4,7-triazaheptane.

(e) 2-(2-Hydroxyethyl)-1,4,7,11-tetraazacyclododecane 2-(2-Benzyloxyethyl)-tris-1,4,7-(4-methyl-benzenesulphonyl)- 1,4,7-triazaheptane (10 mmol) is dissolved in 20 ml dry ethanol and a solution of sodium ethanoate (20 mmol) in 20 ml ethanol is added. The reaction mixture is refluxed for 1 hour, the solvent is evaporated and the residue is taken up in dry dimethylformamide (100 ml); during 15 minutes this solution is added to a solution of diethanolamine tritosylate (10 mmol) (prepared according to the method of Richman et al. J. Am. Chem. Soc. 96 (1974) 2268) in 50 ml dry DMF.

After 2 hours stirring at 110° C. the solution is poured into 150 ml ice water and the solid is collected by filtration and dried in vacuo. The solid is stirred in conc. sulfuric acid and water at 110° C. for 45 hours. The suspension is diluted with 6N hydrochloric acid and THF and after cooling the crystallisate is collected and 2-(2-hydroxyethyl)- 1,4,7,11-tetraazacyclododecane is purified by chromatography.

(f) 2-(2-Hydroxyethyl)-1,4,7,11-tetrakis-carboxymethyl-1,4,7,11-tetraazacyclododecane 2-(2-Hydroxyethyl)-1,4,7,11-tetraazacyclododecane (10 mmol) is dissolved in 50 ml water and the pH is adjusted to 10 using 4M lithium hydroxide solution. Bromoacetic acid lithium salt is added at 60° C. and the pH is kept alkaline while the temperature is gradually increased to 85° C. After 10 hours the solution is loaded on a strong cationic ion exchanger, Biorad AG 50W-X4, and eluted with 6M ammonia in water containing 50 mM ammonium formate. The solution is evaporated and the title compound is purified by chromatography.

EXAMPLE 30

3,6,9-Tris-carboxymethyl-4-(5,6-dihydroxy-3-oxa-hexyl)-3,6,9-triazaundecanediacid (a) 2-(4-(2,2-Dimethyl-1,3-dioxolan-4-yl)-3-oxabutyl)-3-oxo-1,7-bis-triphenylmethyl-1,4,7-triazaheptane First alternative 2-(2-Hydroxyethyl)-3-oxo-1,7-bis-(triphenylmethyl)-1,4,7-triazaheptane (10 mmol, Example 38(a)) is dissolved in dry tetrahydrofuran (50 ml) and 10 mmol sodium hydride is added. When gas evolution stops at ambient temperature, tetrabutylammonium iodide (1 mmol) and 4-bromomethyl-2,2-dimethyl 1,3-dioxolane (10 mmol) is added. After stirring at ambient temperature for 24 hours, the solvent is evaporated, the product is dissolved in ether, the ether phase is washed with water, dried with sodium sulphate, filtered and the solvent evaporated. The product is purified by chromatography on silica.

Second alternative

The method described by J. M. Lacombe et al, Can. J. Chem., 59 (1981) 473 is employed as follows:

2-(2-Hydroxyethyl)-3-oxo-1,7-bis-(triphenylmethyl)-1,4,7-triazaheptane (10 mmol, Example 38(a)) is dissolved in acetonitrile (or alternatively tetrahydrofuran or dimethylformamide) (50 ml) and cooled to −20° C. Trifluoromethylsulfonic acid anhydride (15 mmol) is added, and then a solution of 2,2-dimethyl- 4-hydroxymethyl-1,3-dioxolan (20 mmol) dissolved in the same solvent is added dropwise. After 2 hours at −20° C., the reaction is taken up to ambient temperature and stirred overnight. The solvent is evaporated and the product is purified by chromatography on silica.

(b) 1,5-Diamino-1-(5,6-dihydroxy-3-oxahexyl)-3-azapentane hydrochloride

The product of step (a) is reacted to produce 1,5-diamino-1-(5,6-dihydroxy-3-oxahexyl)-3-azapentane hydrochloride in a process analogous to that of step (c) of Example 38.

(c) 3,6,9-Triscarboxymethyl-4-(5,6-dihydroxy-3-oxahexyl)-3,6,9-triazaundecanediacid The product of step (b) is reacted to produce the title compound in a process analogous to that of step (c) of Example 9.

EXAMPLE 40

Gadolinium (III) chelate of
$N^3,N^6,N^9$-triscarboxymethyl-
4,8-bishydroxymethyl-3,6,9-triazaundecane diacid
disodium salt (a) Gadolinium (III) chelate of
$N^3,N^6,N^9$-tris-carboxymethyl-
4,8-bisbenzyloxymethyl-3,6,9-triazaundecane
diacid-disodium salt $N^3,N^6,N^9$-Triscarboxymethyl-4,8-bis-benzyloxymethyl-3,6,9-triazaundecane diacid (0.50 g, 0.80 mmol) (Example 6) in water (10 ml) was added dropwise to a solution of gadolinium chloride (0.28 g, 0.80 mmol) in water (3 ml) at 70° C. over 30 minutes. The pH was continuously adjusted with sodium hydroxide (2M) to be within the range 5–7. The temperature was increased to 85° C. for 2.5 hours. Gadolinium (III) chelate of $N^3,N^6,N^9$-tris-carboxymethyl-4,8-bisbenzyloxymethyl- 3,6,9-triazaundecane diacid-disodium salt was isolated by evaporation of the clear solution. Yield 0.81 g (99%) of a clear oil containing sodium chloride (0.14 g, 2.4 mmol).

(b) Gadolinium (III) chelate of $N^3,N^6$
,$N^9$-tris-carboxymethyl-
4,8-bishydroxymethyl-3,6,9-triazaundecane
diacid-disodium salt To Gadolinium (III) chelate of $N^3,N^6,N^9$-tris-carboxymethyl- 4,8-bisbenzyloxymethyl-3,6,9-triazaundecane diacid-disodium salt (0.81 g, 0.79 mmol) (containing 0.14 g sodium chloride) in methanol (25 ml) was added ammonium formate (0.30 g) and 10% Palladium on carbon (0.40 g) at 50° C. and the mixture was stirred for 17 hours under a nitrogen atmosphere. The solution was filtered and evaporated. The title compound was isolated as a white powder. Yield 0.56 g (83%) (containing sodium chloride (0.14 g)). M.p. greater than 350° C.

EXAMPLE 41

Bismuth (III) chelate of 3,6-bis-(carboxymethyl)-
4-hydroxyethyl-3,6-diazaoctane diacid
mono-sodium-salt A neutral suspension of bismuth hydroxide was prepared by neutralisation of an acidic solution of bismuth chloride (120 mg, 0.37 mmol, 4 ml) with sodium hydroxide, followed by centrifugation of the precipitate and resuspension of the precipitate in water (4 ml). This solution was added to a neutral solution of 3,6-bis-(carboxymethyl)-4-hydroxyethyl-3,6-diazaoctane diacid (120 mg, 0.37 mmol) (Example 4) in water (4 ml) and the mixture was stirred at 80° C. for 16 hours, and refluxed for 4 hours. The clear solution was evaporated, and the title compound was isolated as a white solid. Yield 200 mg (99%). M.p. 250° C.

EXAMPLE 42

3,9-Bis[N-methyl-(2,3-dihydroxypropylcarbamoyl-
methyl)]- 6-carboxymethyl-4-(2-hydroxyethyl)-
3,6,9-triazaundecane diacid a) 3,9-Bis[N-methyl-(2,3-dihydroxypropyl-
carbamoylmethyl)]- 6-carboxymethyl-4-(2-
acetyloxyethyl)-3,6,9-triazaundecane diacid N-Methylaminopropanediol (0.20 g, 2.5 mmol) was dissolved in dry dimethylacetamide (DMA) (5 ml) and 1-(2-acetyloxyethyl)-1,5-bis(2,6-dioxomorpholino)-3-azapentane- 3-acetic acid (0.5 g, 1.2 mmol) (prepared in accordance with EP-A-299795) was added. The mixture was stirred under nitrogen for 16 hours at ambient temperature. The title compound was precipitated with diethyl ether and chloroform to give a yellow oil. Yield 0.5 g (65%). FAB-MS: 654 (M+1). The structure was confirmed by $^{13}$C NMR.

b) 3,9-Bis[N-methyl-(2,3-dihydroxypropyl-
carbamoylmethyl)]- 6-carboxymethyl-4-(2-
hydroxyethyl)-3,6,9-triazaundecane diacid 3,9-Bis[N-methyl-(2,3-dihydroxypropylcarbamoylmethyl)]- 6-carboxymethyl-4-(2-acetyloxyethyl)-3,6,9-triazaundecane diacid (0.24 g, 0.37 mmol) was dissolved in methanol (20 ml) saturated with ammonia and stirred at ambient temperature overnight. The solvent was evaporated, and the residue was dissolved in water (10 ml) and washed with chloroform (2×10 ml). Evaporation yielded 0.2 g (89%). FAB-MS: 612 (M+1). The structure was confirmed by $^{13}$C NMR.

EXAMPLE 43

6-Carboxymethyl-3,9-bis[N-methyl-(2,3-dihydroxy-
propylcarbamoylmethyl)]-4,8-bis(hydroxy-
methyl)-3,6,9-triazaundecane diacid a) 4,8-Bis(benzyloxymethyl)-6-carboxymethyl-
3,9-bis[N-methyl-(2,3-dihydroxypropyl-
carbamoylmethyl)]-3,6,9-triazaundecane diacid 1,5-Bis(benzyloxymethyl)-1,5-bis(2,6-dioxomorpholino)-3-azapentane- 3-acetic acid (44 g, 73 mmol) was dissolved in dry DMA (200 ml) and added to a solution of N-methylaminopropanediol (15 g, 146 mmol) in dry DMA (200 ml) on an ice bath. The mixture was stirred overnight at ambient temperature, and a solution of diethyl ether/chloroform (1/1) (200 ml) was added. The yellow oil was taken up in water (60 ml) and precipitated with acetone (4000 ml). The title product was isolated as a yellow solid. Yield: 47 g (80%). FAB-MS: 808 (M+1).

b) 6-Carboxymethyl-3,9-bis[N-methyl-(2,3-dihydroxypropylcarbamoylmethyl)]-4,8-bis(hydroxymethyl)-3,6,9-triazaundecane diacid 4,8-Bis(benzyloxymethyl)-6-carboxymethyl-3,9-bis[N-methyl-( 2,3-dihydroxypropylcarbamoylmethyl)]-3,6,9-triazaundecane diacid (40 g, 49 mmol) was dissolved in methanol (2000 ml) and ammonium formiate (23 g, 363 mmol) was added. Palladium on carbon (10%) (64 g) was added under argon, and the suspension was stirred at 50° C. for three hours. The catalyst was filtered off, and the title product was isolated by evaporation of the filtrate. Yield: 29 g (93%). FAB-MS: 628 (M+1).

EXAMPLE 44

6-Carboxymethyl-3,9-bis(dimethylcarbamoylmethyl)-4,8-bis(hydroxymethyl)-3,6,9-triazaundecane diacid a) 4,8-Bis(benzyloxymethyl)-6-carboxymethyl-3,9-bis(dimethylcarbamoylmethyl)-3,6,9-triazaundecane diacid 1,5-Bis(benzyloxymethyl)-1,5-bis(2,6-dioxomorpholino)-3-azapentane- 3-acetic acid (0.2 g, 0.34 mmol) was added to a solution of dimethylamine (40%) in water (10 ml) on an ice bath. The solution was stirred at ambient temperature overnight. The solvent was evaporated and the title product was isolated. Yield 0.23 g (98%). FAB-MS: 688 (M+1).

b) 6-Carboxymethyl-3,9-bis(dimethylcarbamoylmethyl)-4,8-bis(hydroxymethyl)-3,6,9-triazaundecane diacid 4,8-Bis(benzyloxymethyl)-6-carboxymethyl-3,9-bis-(dimethylcarbamoylmethyl)- 3,6,9-triazaundecane diacid (0.02 g, 0.04 mmol) was dissolved in methanol (15 ml) and ammonium formiate (0.02 g, 0.26 mmol) was added. Palladium on carbon (10%) (0.045 g) was added under nitrogen, and the suspension was stirred at 50° C. for three hours. The catalyst was filtered off and washed with methanol (5 ml). The filtrate was evaporated and the title product was isolated. Yield: 0.016 g (90%). FAB-MS: 508 (M+1).

EXAMPLE 45

6-Carboxymethyl-4,8-bis(hydroxymethyl)-3,9-bis(3-oxapentamethylencarbamoylmethyl)-3,6,9-triazaundecane diacid a) 4,8-Bis(benzyloxymethyl)-6-carboxymethyl-3,9-bis(3-oxapentamethylencarbamoylmethyl)-3,6,9-triazaundecane diacid 1,5-Bis(benzyloxymethyl)-1,5-bis(2,6-dioxomorpholino)-3-azapentane- 3-acetic acid (0.2 g, 0.34 mmol) was dissolved in DMA (2 ml) and morpholine (0.6 g, 0.68 mmol) was added, and the solution was stirred at ambient temperature overnight. The solvent was evaporated and the title product was isolated as a yellow oil. Yield: 0.2 g (77%). FAB-MS: 772 (M+1).

b) 6-Carboxymethyl-4,8-bis(hydroxymethyl)-3,9-bis(3-oxapentamethylencarbamoylmethyl)-3,6,9-triazaundecane diacid 4,8-Bis(benzyloxymethyl)-6-carboxymethyl-3,9-bis(3-oxapentamethylencarbamoylmethyl)- 3,6,9-triazaundecane diacid (0.18 g, 0.23 mmol) was dissolved in methanol (20 ml) and ammonium formiate (0.11 g, 1.7 mmol) was added. Palladium on carbon (10%) (0.3 g) was added under nitrogen, and the mixture was stirred at 50° C. for three hours. The catalyst was filtered off and washed with methanol (5 ml). The filtrate was evaporated and the title product was isolated. Yield: 0.12 g (90%). FAB-MS: 592 (M+1).

EXAMPLE 46

6-Carboxymethyl-4,8-bis(hydroxymethyl)-3,9-bis[N-methyl-(5-hydroxy-3-oxapentyl)carbamoylmethyl)]-3,6,9-triazaundecane diacid a) 4,8-Bis(benzyloxymethyl)-6-carboxymethyl-3,9-bis[N-methyl-(5-hydroxy-3-oxapentylcarbamoyl-methyl)]-3,6,9-triazaundecane diacid 1,5-Bis(benzyloxymethyl)-1,5-bis(2,6-dioxomorpholino)-3-azapentane- 3-acetic acid (0.2 g, 0.34 mmol) was dissolved in DMA (2 ml) and added to a solution of N-methyl- 2-(2-hydroxyethoxy)ethylamine (0.08 g, 0.68 mmol) in DMA (0.5 ml). The solution was stirred overnight at ambient temperature, the solvent evaporated and the title product was isolated as a yellow oil. Yield: 0.12 g (44%). FAB-MS: 836 (M+1).

b) 6-Carboxymethyl-4,8-bis(hydroxymethyl)-3,9-bis[N-methyl-(5-hydroxy-3-oxapentylcarbamoylmethyl)]-3,6,9-triazaundecane diacid 1,5-Bis(benzyloxymethyl)-6-carboxymethyl-3,9-bis[N-methyl-( 5-hydroxy-3-oxa-pentyl)-carbamoylmethyl)]-3,6,9-triazaundecane diacid (0.12 g, 0.14 mmol) was dissolved in methanol (20 ml) and ammonium formiate (0.07 g, 1.6 mmol) was added. Palladium on carbon (10%) (0.19 g) was added under argon, and the suspension was stirred at 50° C. for three hours. The catalyst was filtered off and washed with methanol. The filtrate was evaporated and the title product was isolated. Yield: 0.09 g (95%). FAB-MS: 656 (M+1).

EXAMPLE 47

6-Carboxymethyl-4-(2-hydroxyethyl)-3,9-bis[N-methyl-(5-hydroxy-3-oxapentylcarbamoylmethyl)]-3,6,9-triazaundecane diacid a) 4-(2-Acetyloxyethyl)-6-carboxymethyl-3,9-bis[N-methyl-(5-hydroxy-3-oxapentyl-carbamoylmethyl)]-3,6,9-triazaundecane diacid 1-(2-Acetyloxyethyl)-1,5-bis-(2,6-dioxomorpholino)-3-azapentane- 3-acetic acid (0.14 g, 0.34 mmol) is dissolved in DMA and added to a solution of N-methyl-2-(2-hydroxyethoxy)ethylamine (0.08 g, 0.68 mmol) in DMA. The solution is stirred overnight at ambient temperature, the solvent is evaporated and the title product is isolated.

b)
6-Carboxymethyl-4-(2-hydroxyethyl)-3,9-bis[N-methyl-(5-hydroxy-3-oxapentylcarbamoylmethyl)]-3,6,9-triazaundecane diacid 4-(2-Acetyloxyethyl)-6-carboxymethyl-3,9-bis[N-methyl-( 5-hydroxy-3-oxapentylcarbamoylmethyl)]-3,6,9-triazaundecane diacid is dissolved in methanol saturated with ammonia and stirred overnight at ambient temperature. The solvent is evaporated. The oil is taken up in water and washed with chloroform. The water is evaporated and the title product is isolated.

EXAMPLE 48

6-Carboxymethyl-4,8-bis(hydroxymethyl)-3,9-bis-(3-hydroxypentamethylencarbamoylmethyl)-3,6,9-triazaundecane diacid a) 4,8-Bis-benzyloxymethyl-6-carboxymethyl-3,9-bis(3-hydroxypentamethylencarbamoylmethyl)-3,6,9-triazaundecane diacid 1,5-Bis(benzyloxymethyl)-1,5-bis(2,6-dioxomorpholino)-3-azapentane- 3-acetic acid (0.2 g, 0.34 mmol) is dissolved in DMA and added to a solution of 4-hydroxypiperidine (0.7 g, 0.68 mmol) in DMA. The solution is stirred overnight at ambient temperature, the solvent evaporated and the title product is isolated.

b) 6-Carboxymethyl-4,8-bis(hydroxymethyl)-3,9-bis-(3-hydroxypentamethylencarbamoylmethyl)-3,6,9-triazaundecane diacid 1,5-Bis(benzyloxymethyl)-6-carboxymethyl-3,9-bis(3-hydroxypentamethylencarbamoylmethyl)- 3,6,9-triazaundecane diacid (0.11 g, 0.14 mmol) is dissolved in methanol and ammonium formiate (0.07 g, 1.6 mmol) is added. Palladium on carbon (10%) (0.19 g) is added under argon, and the suspension is stirred at 50° C. for three hours. The catalyst is filtered off and washed with methanol. The filtrate is evaporated and the title product is isolated.

EXAMPLE 49

6-Carboxymethyl-4-(2-hydroxyethyl)-3,9-bis(pentamethylencarbamoylmethyl)-3,6,9-triazaundecane diacid a) 4-(2-Acetyloxyethyl)-6-carboxymethyl-3,9-bis(pentamethylencarbamoylmethyl)-3,6,9-triazaundecane diacid 1-(2-Acetyloxyethyl)-1,5-bis(2,6-dioxomorpholino)-3-azapentane- 3-acetic acid (0.14 g, 0.34 mmol) is dissolved in DMA and added to a solution of piperidine (0.06 g, 0.68 mmol) in DMA. The solution is stirred overnight at ambient temperature, the solvent is evaporated and the title product is isolated.

b) 6-Carboxymethyl-4-(2-hydroxyethyl)-3,9-bis(pentamethylencarbamoylmethyl)-3,6,9-triazaundecane diacid 4-(2-Acetyloxyethyl)-6-carboxymethyl-3,9-bis-(pentamethylencarbamoylmethyl)- 3,6,9-triazaundecane diacid (0.10 g, 0.16 mmol) is dissolved in methanol saturated with ammonia and stirred overnight at ambient temperature. The solvent is evaporated. The oil is taken up in water and washed with chloroform. The water is evaporated and the title product is isolated.

EXAMPLE 50

Gadolinium(III) chelate of 3,9-bis[N-methyl-(2,3-dihydroxypropyl-carbamoylmethyl)]-6-carboxymethyl-4-(2-hydroxyethyl)-3,6,9-triazaundecane diacid The bis-amide from Example 42 (0.33 g, 0.54 mmol) was dissolved in water (10 ml), gadolinium(III) oxide (0.10 g, 0.27 mmol) was added and the mixture was refluxed overnight. The water was evaporated off and the title compound was isolated as a light yellow solid. Yield 0.4 g (96%), FAB-MS: 767 (M+1).

EXAMPLE 51

Gadolinium(III) chelate of 6-carboxymethyl-3,9-bis[N-methyl-(2,3-dihydroxypropylcarbamoylmethyl)]-4,8-bis-(hydroxymethyl)-3,6,9-triazaundecane acid 6-Carboxymethyl-3,9-bis[N-methyl-(2,3-dihydroxypropylcarbamoylmethyl)]- 4,8-bis(hydroxymethyl)-3,6,9-triazaundecane diacid (15.6 g, 24.8 mmol) (Example 43) was dissolved in water (250 ml) and gadolinium(III) chloride (8.83 g, 24.8 mmol) was added. The pH was adjusted to 6.4 with 5M NaOH (5 ml). The solution was stirred at ambient temperature for 15 minutes, filtered and the solvent was evaporated. The crude product was treated 3 times with methanol (3×30 ml) to remove inorganic salts. The suspension was filtered, the filtrate was evaporated and the title product was isolated. Yield: 18.4 g (95%). FAB-MS: 783 (M+1).

EXAMPLE 52

Dysprosium(III) chelate of 6-carboxymethyl-3,9-bis[N-methyl-(2,3-dihydroxypropylcarbamoylmethyl)]-4,8-bis(hydroxymethyl)-3,6,9-triazaundecane diacid 6-Carboxymethyl-3,9-bis[N-methyl-(2,3-dihydroxypropylcarbamoylmethyl)]- 4,8-bis(hydroxymethyl)-3,6,9-triazaundecane diacid (0.15 g, 0.24 mmol) (Example 43) was dissolved in water (10 ml), dysprosium(III) oxide (0.45 g, 0.12 mmol) was added and the mixture was stirred at 80° C. for 8 hours. The solution was filtered, the solvent evaporated and the title product was isolated. Yield: 0.19 g (99%). FAB-MS: 788 (M+1).

EXAMPLE 53

Bismuth(III) chelate of 6-carboxymethyl-3,9-bis[N-methyl-(2,3-dihydroxypropylcarbamoylmethyl)]-4,8-bis(hydroxymethyl)-3,6,9-triazaundecane diacid A neutral suspension of bismuth(III) hydroxide is prepared by neutralisation of a solution of bismuth(III) chloride (0.1 g, 0.52 mmol, 4 ml) with sodium hydroxide, followed by centrifugation of the precipitate and resuspension of the precipitate in water (4 ml). This solution is added to a neutral solution of 6-carboxymethyl- 3,9-bis[N-methyl-(2,3-dihydroxypropylcarbamoylmethyl)]- 4,8-bis(hydroxymethyl)-3, 6,9-triazaundecane diacid (0.2 g, 0.32 mmol) (Example 43) in water (4 ml) and the mixture is refluxed for 4 hours. The clear solution is evaporated, and the title product is isolated.

EXAMPLE 54

Preparation of a solution containing the gadolinium(III) chelate of 6-carboxymethyl-3,9-bis[N-methyl-(2,3-dihydroxypropylcarbamoylmethyl)]-4,8-bis(hydroxymethyl)-3,6,9-triazaundecane diacid Gadolinium(III) chelate of 6-carboxymethyl-3,9-bis[N-methyl-(2,3-dihydroxypropylcarbamoylmethyl)]-4,8-bis(hydroxymethyl)-3,6,9-triazaundecane diacid (7.82 g, 10 mmol) (Example 51) was dissolved in 20 ml water. The solution was filtered, filled in a 20 ml vial and autoclaved. The solution contained 0.5 mmol gadolinium per ml.

EXAMPLE 55

Preparation of a solution containing the trisodium salt of 6-carboxymethyl-3,9-bis[N-methyl-(2,3-dihydroxypropylcarbamoylmethyl)]-4,8-bis(hydroxymethyl)-3,6,9-triazaundecane diacid 6-Carboxymethyl-3,9-bis[N-methyl-(2,3-dihydroxypropylcarbamoylmethyl)]- 4,8-bis(hydroxymethyl)-3,6,9-triazaundecane diacid (1.88 g, 3 mmol) (Example 43) was dissolved in water (15 ml), the pH was adjusted to 7 by careful addition of 1M sodium hydroxide, water was added to 20 ml, the solution was filtered and filled into a 20 ml vial. The vial was autoclaved.

The solution contained 0.15 mmol of the trisodium salt of 6-carboxymethyl-3,9-bis[N-methyl-(2,3-dihydroxypropylcarbamoylmethyl)]- 4,8-bis(hydroxymethyl)- 3,6,9-triazaundecane diacid per ml.

The solution is for the treatment of acute of chronic poisoning by heavy metals such as lead.

EXAMPLE 56

Vial containing the technetium chelate of 6-carboxymethyl-3,9-bis[N-methyl-(2,3-dihydroxypropylcarbamoylmethyl)]-4,8-bis(hydroxymethyl)-3,6,9-triazaundecane diacid A vial is filled with 6-carboxymethyl-3,9-bis[N-methyl-(2,3-dihydroxypropylcarbamoylmethyl)]-4,8-bis(hydroxymethyl)- 3,6,9-triazaundecane diacid (4 mg) (Example 43) and tin(II) chloride (0.22 mg) as dry powder.

A solution of $^{99m}$Tc as pertechnetate in 0.9% sterile sodium chloride solution should be added before use. The technetium chelate with 6-carboxymethyl-3,9-bis[N-methyl-( 2,3-dihydroxypropylcarbamoylmethyl)]-4,8-bis(hydroxymethyl)- 3,6,9-triazaundecane diacid is for scintigraphic examination of organs such as the brain and kidneys. The chelate is also useful for study of kidney function.

EXAMPLE 57

Preparation of a solution containing the sodium salt of the zinc(II) chelate of 6-carboxymethyl-3,9-bis[N-methyl-(2,3-dihydroxypropylcarbamoylmethyl)]-4,8-bis(hydroxymethyl)-3,6,9-triazaundecane diacid 6-Carboxymethyl-3,9-bis[N-methyl-(2,3-dihydroxypropylcarbamoylmethyl)]- 4,8-bis(hydroxymethyl)-3,6,9-triazaundecane diacid (1.26 g, 2 mmol) (Example 43) and zinc(II) carbonate (0.25 g, 2 mmol) were refluxed for 12 hours in water (15 ml). The mixture was cooled to ambient temperature, the pH was adjusted to 6 by careful addition of 1M sodium hydroxide, water was added to 20 ml, the solution was filtered and filled into a 20 ml vial. The vial was autoclaved. The solution contained 0.1 mmol of the zinc chelate as its sodium salt per ml.

The solution is for the treatment of acute or chronic poisoning by heavy metals or radioactive metals such as plutonium.

We claim:

1. A method of generating enhanced images of the human or non-human animal body, which method comprises administering to said body a diagnostic agent and generating an X-ray, MR-diagnostics, ultrasound or scintigraphic image of at least a part thereof, wherein the diagnostic agent comprises a metal chelate, whereof the chelating entity is a residue of formula (III)

$$(X-CHR_1^*)_2-N-(CHR_1)_n(NY-(CHR_1)_m)_x-N-(CHR_1^*X)_2 \quad (III)$$

(wherein x is 0 or 1;

Y is a group $-(CHR_1)_p-N(CHR_1^*X)_2$ or a group $-CHR_1^*X$;

n, m and p are each 2, 3 or 4;

each group X, which may be the same or different, is a group $R_1^*$ or a carboxyl group or a derivative thereof selected from the group consisting of amide, ester and carboxylate salt groups;

each group $R_1$ or $R_1^*$, which may be the same or different, is a hydrogen atom, a hydroxyalkyl group or an optionally hydroxylated alkoxy or alkoxyalkyl group, with the provisos that at least two nitrogens carry a $-CHR_1^*X$ moiety wherein X is a carboxyl group or a derivative thereof selected from the group consisting of amide, ester and carboxylate salt groups, that each $-CHR_1^*X$ moiety is other than methyl and that either at least one $R_1$ group is other than hydrogen or three of the X groups are carboxyl groups or derivatives thereof selected from the group consisting of amide, ester and carboxylate salt groups and the remaining X groups are hydroxylated alkoxy or alkyl groups) or a salt thereof, together with at least one pharmaceutical or veterinary carrier or excipient.

2. A method as claimed in claim 1 wherein in said residue of formula III at least one $R_1$ group is other than hydrogen, or a metal chelate or salt thereof.

3. A method as claimed in claim 1 wherein in said residue of formula III at least two $R_1$ groups each represent other than hydrogen, or a metal chelate or salt thereof.

4. A method as claimed in claim 1 wherein said chelating entity of said metal chelate is a residue of formula $$(X-CHR_1^*)_2-N-(CHR_1)_2-NY-(CHR_1)_2-N-(CHR_1^*X)_2$$

wherein X, $R_1^*$, $R_1$ and Y are as defined in claim 1, or a salt or metal chelate thereof.

5. A method as claimed in claim 1 wherein in said residue of formula III the $R_1$ and $R_1^*$ moieties, which may be the same or different, are hydrogen, $C_{1-8}$alkoxy, polyalkoxy, hydroxyalkyl, polyhydroxyalkyl, polyhydroxyalkoxy, hydroxyalkoxyalkyl or hydroxypolyalkoxy groups, or a salt or metal chelate thereof.

6. A method as claimed in claim 1 wherein said residue of formula III is selected from the group consisting of:
3,6-bis-(carboxymethyl)-4-hydroxyethyl-3,6-diazaoctane diacid;

3,6,9-tris-carboxymethyl-4-(2-hydroxyethyl)-3,6,9-triazaundecane diacid;

3,9-bis(methylcarbamoylmethyl)-6-carboxymethyl-4-(2-hydroxyethyl)- 3,6,9-triazaundecane diacid;

3,6,9-tris-carboxymethyl-4-(5,6-dihydroxy-3-oxa-hexyl)- 3,6,9-triazaundecane diacid;

N-carboxymethyl-N,N-bis((N'-carboxymethyl-N'-2,3-dihydroxypropyl)- 2-aminoethyl)-amine;

N,N,N-tris-((N'-carboxymethyl-N'-2,3-dihydroxypropyl)-2-aminoethyl)-amine;

or a salt or metal chelate thereof.

7. A method as claimed in claim 1 wherein said chelate is a paramagnetic metal chelate.

* * * * *